United States Patent
Reynolds et al.

(10) Patent No.: US 10,266,408 B2
(45) Date of Patent: *Apr. 23, 2019

(54) MODULAR BIOCOMPATIBLE MATERIALS FOR MEDICAL DEVICES AND USES THEREOF

(71) Applicant: Colorado State University Research Foundation, Fort Collins, CO (US)

(72) Inventors: Melissa M. Reynolds, Fort Collins, CO (US); Benjamin P. Reynolds, Fort Collins, CO (US)

(73) Assignee: COLORADO STATE UNIVERSITY RESEARCH FOUNDATION, Fort Collins, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/597,832

(22) Filed: Jan. 15, 2015

(65) Prior Publication Data

US 2015/0118268 A1    Apr. 30, 2015

Related U.S. Application Data

(63) Continuation of application No. 14/192,691, filed on Feb. 27, 2014, now Pat. No. 9,493,352, which is a continuation of application No. 12/979,927, filed on Dec. 28, 2010, now Pat. No. 8,771,756.

(60) Provisional application No. 61/290,316, filed on Dec. 28, 2009.

(51) Int. Cl.
| | |
|---|---|
| A61K 33/00 | (2006.01) |
| A61L 29/14 | (2006.01) |
| A61L 31/06 | (2006.01) |
| A61L 31/16 | (2006.01) |
| A61L 31/14 | (2006.01) |
| A61L 29/16 | (2006.01) |
| A61L 29/06 | (2006.01) |
| C01B 21/26 | (2006.01) |
| A61L 27/54 | (2006.01) |
| C01B 21/24 | (2006.01) |

(52) U.S. Cl.
CPC ............ *C01B 21/265* (2013.01); *A61K 33/00* (2013.01); *A61L 27/54* (2013.01); *A61L 29/06* (2013.01); *A61L 29/146* (2013.01); *A61L 29/16* (2013.01); *A61L 31/06* (2013.01); *A61L 31/146* (2013.01); *A61L 31/16* (2013.01); *C01B 21/24* (2013.01); *A61L 2300/114* (2013.01); *A61L 2300/608* (2013.01)

(58) Field of Classification Search
None
See application file for complete search history.

(56) References Cited

U.S. PATENT DOCUMENTS

| | | | |
|---|---|---|---|
| 5,648,508 A | 7/1997 | Yaghi | |
| 6,887,485 B2 | 5/2005 | Fitzhugh et al. | |
| 7,087,709 B2 | 8/2006 | Stamler et al. | |
| 7,128,904 B2 | 10/2006 | Batchelor et al. | |
| 7,335,383 B2 | 2/2008 | Meyerhoff et al. | |
| 7,637,983 B1* | 12/2009 | Liu ..................... | B01D 53/228 210/500.21 |
| 7,763,283 B2 | 7/2010 | Batchelor et al. | |
| 8,007,857 B1 | 8/2011 | Hossainy | |
| 8,771,756 B2 | 7/2014 | Reynolds et al. | |
| 2004/0087510 A1 | 5/2004 | Garvey et al. | |
| 2004/0224868 A1 | 11/2004 | Meyerhoff et al. | |
| 2005/0220756 A1 | 10/2005 | Stamler et al. | |
| 2005/0265958 A1 | 12/2005 | West et al. | |
| 2006/0153795 A1 | 7/2006 | West et al. | |
| 2008/0226686 A1 | 9/2008 | Meyerhoff et al. | |
| 2008/0255101 A1 | 10/2008 | Garvey et al. | |
| 2009/0118819 A1 | 5/2009 | Merz et al. | |
| 2010/0285100 A1* | 11/2010 | Balkus, Jr. ............ | A61K 33/00 424/445 |
| 2011/0159116 A1 | 6/2011 | Reynolds et al. | |
| 2014/0178504 A1 | 6/2014 | Reynolds et al. | |

FOREIGN PATENT DOCUMENTS

| | | |
|---|---|---|
| EP | 2083946 B1 | 8/2009 |
| FR | 2929278 A1 | 10/2009 |
| WO | WO2008020218 A1 | 2/2008 |
| WO | 2012116177 A2 | 8/2012 |

OTHER PUBLICATIONS http://www.plasticfantasticlibrary.com/library/plastic/156/polyoxybenzylmethylenglycolanhydride.html, "Plastic Fantastic Library Entry for polyoxybenzylmethylenglycolanhydride (Bakelite)" Accessed Aug. 1, 2018, no pagination.*
Dinca et al., Observation of Cu2-H2 Interactions in a Fully Desolvated Sodalite-Type Metal-Organic Framework, Angewandte Chem., Int. Ed., 2007, 46, pp. 1419-1422.
Liu et al. "Preparation and characterization of an improved Cu2+-cyclen polyurethane material that catalyzes generation of nitric oxide from S-nitrosothiols", J Mater Chem. Jan. 1, 2012; 22(36): 18784-18787.
Shin et al. Improving the biocompatibility of in vivo sensors via nitric oxide release, The Analyst, 2006, 131, pp. 609-615.
Third Party Observations issued in EP Application No. 10 80 3195.6, mailed Jul. 13, 2015, 3 pages.
Trafton, Anne; Nitric Oxide shown to cause colon cancer, MIT News, 2009, (http://newsoffice.mit.edu/2009/colon-cancer-0119).

(Continued)

*Primary Examiner* — Mina Haghighatian
*Assistant Examiner* — Erin Hirt
(74) *Attorney, Agent, or Firm* — Faegre Baker Daniels LLP

(57) ABSTRACT

A metal-organic compound containing polymer matrix includes a polymer and a three-dimensional metal-organic framework includes a polydentate organic linker. The metal-organic compound containing polymer matrix is configured to continuously produce nitric oxide when exposed to a physiological fluid including a nitric oxide-releasing compound via a catalytic reaction catalyzed by the three-dimensional metal-organic framework.

16 Claims, 6 Drawing Sheets

(56) References Cited

OTHER PUBLICATIONS

Allendorf, Mark D. et al., "Plasmonic Devices and Sensors Built from Ordered Nanoporous Materials", Sandia Report, SAND2009-5964, Unlimited Release, Printed Sep. 2009, Sandia National Laboratories, 40 pages.
Alsadoni, H. H., "S-Nitrosothiols as Nitric Oxide-Donors: Chemistry, Biology and Possible Future Theraputic Applications". Current Medicinal Chemistry 2004, 11, 2679-2690.
Askew, S. C. et al., "Catalysis by Cu2+ of nitric oxide release from S-nitrosothiols (RSNO)", Journal of the Chemical Society Perkin Transaction 2, 1995, 8, 741-745.
Bordiga, S. et al., "Adsorption Properties of HKUST-1 Toward Hydrogen and Other Small Molecules Monitored by IR", Physical Chemistry Physics, vol. 9, 2007, pp. 2676-2685.
Britt, David et al., "Ring-Opening Reactions Within Porous metal—Organic Frameworks", Inorg. Chem. 2010, 49, 6387-6389.
Chen, Banglin et al., "A Microporous Metal-organic Framework for Gas-Chromatographic Separation of Alkanes", Angew. Chem. 2006, 118, pp. 1418-1421.
Chui, S. et al., "A Chemically Functionalizable Nanoporous Material Cu3TMA2H2O3", Science 1999, vol. 283, pp. 1149-1150.
Demessence, A. et al., "Strong CO2 Binding in a Water-Stable, Triazolale-Bridged Metala Organic Framework Functionalized with Ethylenediamine", Journal of the American Chemical Society, 2009, 131 (25), 8784-8786.
Dicks, A. P. et al., "Decomposition of S-nitrosothiols: the effects of added thiols", Journal of the Chemical Society Perkin Transactions 1997, pp. 1429-1434.
Dicks. A. P. et al., "Generation of nitric oxide from S-nitrosothiols using protein bound Cu2+ sources", Chemistry & Biology 1996, vol. 3, 655-659.
Dicks, Andrew P. et al., "Identification of Cu as the effective reagent in nitric oxide formation from S-nitrosothiols (RSNO)", J. Chem. Soc., Perkin Trans. 2, 1996, pp. 481-487.
Drago, R. S. et al., "The Reaction of Nitrogen (II) Oxide with Diethylamine", Journal of the American Chemical Society, 1960, 82, 96-98.
Drago, R.S. et al., "The Reaction of Nitrogen (II) Oxide with Various Primary and Secondary Amines", Journal of the American Chemical Society, 1961, 83, 1819-1822.
Eddaoudi, M. et al., "Modular Chemistry: Secondary Building Units as a Basis for the Design of Highly Porous and Robust Metal Organic Carboxylate Frameworks", Acc. Chem. Res., 2001, 34, 319-330.
Ene, Cristian D. et al., "One-dimensional and two-dimensional coordination polymers constructed from copper(II) nodes and polycarboxylato spacers: synthesis, crystal structures and magnetic properties", Polyhedron 27(2008) 574-582.
Fleser, P. S. et al., "Nitric oxide-releasing biopolymers inhibit thrombus formation in a sheep model of arteriovenous bridge grafts", Journal of Vascular Surgery 2004, vol. 40 No. 4, 803-811.
Frost, M. C. et al., "Polymers incorporating Nitic Oxide Releasing/Generating Substances for Improved Biocompatibility of Blood-Contacting Medical Devices", Biomaterials 2005, 26, 1685-1693.
Furuyama, Shozo et al., "Physisorption of Nitric Oxide, Carbon Monoxide, Nitrogen, and Oxygen by Magnesium Oxide Powder", The Journal of Physical Chemistry, vol. 28, No. 9, 1978, pp. 1029-1032.
Garibay, Sergio J. et al., "Postsynthetic Modification: A Versatile Approach Toward Multifunctional Metal-Organic Frameworks", Inorg. Chem. 2009, 48,7341-7349.
Harding, Jacqueline L. et al., "Metal Organic Frameworks as Nitric Oxide catalysts", J. Am. Chem. Soc. 2012, 134(7), pp. 3330-3333.
Hart, T. W., "Some Observations Concerning the S-nitroso and S-phenylsulphonyl Derivatives of L-cysteine and Glutathione", Tetrahedron Letters 1985, 26 (16), 2013-2016.

Herm, Zoey R. et al., "Metal-Organic Frameworks as Adsorbents for Hydrogen purification and precombustion Carbon Dioxide Capture", Journal of the American Chemical Society, 2011, vol. 133, pp. 5664-5667.
Hrabie, J. A. et al., "New Nitric Oxide Releasing Zwitterions Derived from Polyamines", Journal of Organic Chemistry 1993, 58, 1472-1476.
Ignarro, Louis J. et al., "Nitric Oxcide Donors and Cardiovascular Agents Modulating the Bioactivity of Nitric Oxcide: An Overview", Cirrulation Research, Jan. 2002, 90, pp. 21-28.
Ingleson, Michael J. et al., "Nitric Oxide Chemisorption in a Postsynthetically Modified metal—Organic Framework", Inorg. Chem. 2009, 48, 9986-9988.
International Preliminary Report on Patentability issued in PCT/US2012/026317, dated Mar. 18, 2014, 6 pages.
International Search Report and Written Opinion issued in PCT/US2010/062229, dated Apr. 15, 2011, 9 pages.
International Search Report and Written Opinion issued in PCT/US2012/026317 dated Dec. 6, 2012. 10 pages.
Isaeva, V.I. et al., "The Application of Metal-Organic Frameworks in Catalysis (Review)", Petroleum Chemistry, 2010, vol. 50, No. 3, pp. 167-180.
James, S. L. et al. et al., "Metal Organic frameworks", Chemical Society Reviews, 2003, 32, 276-288.
Kitagawa, Susumu et al., "Functional Porous Coordination Polymers", Angew. Chem. int. Ed 2004, 43, 2334-2375.
Li, H. et al., "Design and Synthesis of an exceptionally stable and highly porous metal organic framework", Nature 1999, vol. 402, pp. 276-279.
McKinlay, Alistair C. et al., "Exceptional Behavior over the Whole Adsorption—Storage—Delivery Cycle for NO in Porous Metal Organic Frameworks", J. Am. Chem. Soc. 2008, 130, 10440-10444.
McKinlay, Alistair C. et al., "Exceptional Behavior Over the Whole Adsorption Storage Delivery cycle for NO in Porous Metal Organic Frameworks", Journal of the American Chemical Society, vol. 130, 2008, pp. 10440-10444.
Nguyen, J. G. et al., "Moisture-Resitant and Superhydrophobic Metal-Organic Frameworks Obtained via Postsynthetic Modification", Journal of the American Chemical Society, 2010, 132, 4560-4561.
Noble, D. R. et al., "Structure Reactivity Studies of the Cu2 plus catalyzed Decomposition of Four S Nitrosothiols Based around the S NitrocysteineS Nitrosoglutathione Structures", Nitric Oxide: Biology and Chemistry, 2000, 4 (4), 392-398.
Oh, B. K. et al., "Spontaneous Catalytic Generation of Nitric Oxide from S-Nitrosothiols at the Surface of Polymer Films Doped with Lipophilic Copper(II) Complex", Journal of the American Chemical Society, 2003, 125, 9552-9553.
Palmer, R.M.J. et al., "Vascular endothelial cells synthesize nitric oxide from L-arginine", Nature, vol. 333, Jun. 16, 1988, pp. 664-666.
Prakash, M. Jaya et al., "Metal-organic macrocycles, metal-organic polyhedra and metal-organic frameworks", Chem. Commun., 2009, 3326-3341.
Puiu, S. C. et al, "Metal Ion-Mediated Nitric Oxide Generation From Polyurethanes via Covalently linked CopperII Cyclen Moieties", Journal of Biomedical Materials Research Part B Applied Biomaterials, 2009, 203-212.
Qiu, Shilun et al., "Molecular engineering for synthesizing novel structures of metal-organic frameworks with multifunctional properties", Coordination Chemistry Reviews 253 (2009) 2891-2911.
Schlichte, K. et al., Improved Synthesis, thermal stability and catalytic properties of the metal organic framework compound Cu3BTC2, Micropourous and Mesoporous Materials, 2004, 73, 81-88.
Seabra, Amedea B. et al., "Nitric Oxcide-Releasing vehicles for Biomedical Applications", Journal of Materials Chemistry, published 2010, 20, pp. 1624-1637.
Smith, D. J. et al., "Nitric Oxide releasing polymers Containing the NONO Group", Journal of Medicinal Chemistry, 1999, 39, 1148-1156.

(56) References Cited

OTHER PUBLICATIONS

Tanabe, K. K. et al., "Systematic Functionalization of a Metal Organic Framework via a Postsynthetic Modification Approach", Journal of the American Chemical Society, 2008, 130, 8508-8517.
Wang, Z. et al., "Post Synthetic Modification of Metal Organic Frameworks", Chemical Society Reviews, 2009, 38, 1315-1329.
Williams, L. H. et al., "The Chemistry of S-Nitrosothiols", Accounts of Chemical Research, 1999, 32, 869-876.
Xiao, Bo et al., "High Capacity Hydrogen and Nitric Oxcide Adsorption and Storage in a Metal-Organic Framework", Journal American Chemical Society, vol. 129, No. 5, 2007, pp. 1203-1209.
Xiao, Bo et al., "High-Capacity Hydrogen and Nitric Oxide Adsorption and Storage in a Metal Organic Framework", Journal of the American Chemical Society, American Chemical Society, US, vol. 129, No. 5, Feb. 7, 2007, pp. 1203-1209.
Yaghi, O. M. et al., "Reticular Synthesis and the Design of new Materials", Nature 2003, vol. 423, pp. 705-714.
Yaghi, O. M. et al., "Synthetic Strategies, Structure Patterns, and Emerging Properties in the Chemistry of Modular Porous Solids", Accounts of Chemical Research 1998, vol. 31 No. 8, pp. 474-484.

* cited by examiner

MODULAR BIOCOMPATIBLE MATERIALS FOR MEDICAL DEVICES AND USES THEREOF

CROSS-REFERENCE TO RELATED APPLICATIONS

This application is a continuation of U.S. application Ser. No. 14/192,691, filed Feb. 27, 2014, entitled "Modular Biocompatible Materials for Medical Devices and Uses Thereof," now U.S. Pat. No. 9,493,352, which is a continuation of U.S. application Ser. No. 12/979,927, filed Dec. 28, 2010, entitled Biocompatible Materials for Medical Devices, now U.S. Pat. No. 8,771,756, which claims benefit of U.S. Provisional Patent Application No. 61/290,316, filed Dec. 28, 2009, incorporated herein by reference in their entirety.

BACKGROUND

Each year billions of health care dollars are spent on medical devices that fail in clinical practice (e.g., intravascular and neonatal catheters, coronary artery and vascular stents and grafts, guidewires, extracorporeal membrane oxygenation, circuits, heart valves, by-pass circuits, etc.). These device failures are due to the introduction of a foreign material into the body leading to a multitude of serious health risks and undesirable complications including thrombosis, inflammation, cell proliferation, infection, and tissue overgrowth on the surface of the implanted device. Over the last 50 years, much has been learned about these device failures and attempts have been made to prevent failures using (1) alternative systemic drug therapies, (2) surface modifications on the device, or (3) a combination of both, approaches.

Despite efforts to improve the efficacy of body-contacting and implantable medical devices, the incompatibility of materials within human blood and tissue still causes serious complications in patients. Thus, systemic or regional drug therapies remain necessary (e.g., use of heparin, for short-term anticoagulation applications). Most often, when these drugs are administered they produce a systemic response in the patient. Systemic responses can mask blood chemistry problems and lead to a greatly increased possibility of complications and morbidity. Research studies examining alternative mechanisms are ongoing, but there is not yet an FDA-approved alternative material that overcomes all the problems associated with body-material interactions and systemic drug therapies. As such, in clinical practice today, all implanted devices eventually fail.

To approach the aforementioned shortcomings, it is worth considering the structure and function of the ideal blood-contacting material. Preferably this material would simultaneously inhibit multiple pathways of device complication (i.e., thrombosis, inflammation, cell proliferation and migration, restenosis as well as infection) but without causing systemic side effects of its own. Such a material strategy requires not only the identification of suitable therapeutic agent(s) with appropriate biological half-lives, but the approach also requires the material's architecture to be fabricated and tailored specifically to the needs of the clinical application. Thus, the approach to an ideal body-contacting material requires a biomaterial that can be systematically and dramatically tailored for use in a wide variety of devices while promising the simultaneous reduction in complicating factors. Currently, no material substrates exist that can be modified in such diverse ways without significantly altering the chemical, physical, or cytotoxicity properties of the material and, in turn, rendering the material unsuitable for clinical use. A modular biomaterial that can simultaneously reduce or eliminate thrombosis, inflammation, cell proliferation, and infection, and also attenuate normal tissue growth upon exposure to physiological fluid, such as blood, is paramount to improve and advance the efficacy of medical devices.

Nitric oxide is a free radical that is produced naturally by the body in several ways. Among these processes, the release and function of NO in endothelial cells (EC) has been the most extensively studied. For example, the endothelial ceils that line all blood vessel walls produce NO via nitric oxide synthase (NOS) by the oxidation of L-arginine. The continuous release of NO from the EC has been shown to contribute significantly to the exceptional thromboresistivity and vascular function of a healthy vessel. For thromboresistivity, NO released from the EC into the blood stream temporarily "anesthetizes" any platelets that come close to the surface, preventing platelet adhesion and activation. In addition, NO prevents the formation of thrombi at sites of vascular injury and thus favors the dissolution of clot.

At the same time, NO produced by the ECs also diffuses into the underlying smooth muscle cells and acts as a vasoregulatory molecule. Results of in vivo studies have demonstrated that NO inhibits neointimal hyperplasia and causes vasorelaxation of surrounding cells. Because of these findings, agents that release nitric oxide have already been suggested as a potential pharmacological strategy for reducing intimal hyperplasia following balloon angioplasty procedures. In addition, researchers have shown NO as an effector in wound healing mechanisms and as an important regulator of angiogenesis and revascularization. Furthermore NO has been implicated in the control of sepsis, the treatment of tumors, neurotransmission, bone growth, and reproduction.

Despite the known uses of NO, NO materials that can be used clinically to release therapeutic amounts of NO at levels required to prevent thrombosis, restenosis, inflammation, and infection have not been reported. A primary problem with current approaches to incorporating NO therapeutic agents into medical devices is that the materials provide inadequate NO loading dosages. As a result, the currently available materials limit the length of time for useful NO fluxes to only a few days in most systems. While this may be suitable for some limited short-term medical applications, it is not viable for most implanted and blood-contacting medical devices. While this may be suitable for some limited short-term medical applications, it is not viable for most implanted and fluid-, tissue-, or cell-contacting, medical devices, such as blood-contacting medical devices.

A significant cause of this issue is the structure and type of compound substrate upon which the NO moiety is currently attached. These substrates are organic compounds that are chemically limited in their capacity for loading NO and their ability to be structurally modified. High degrees of modification in the organic substrates to attempt to increase the NO loading amounts often lead to major changes in the physical, chemical, and mechanical properties of the material and render the material unsuited for use in medical applications. Further, many of these organic substrates are prone to decomposition, especially under physiological conditions, which leads to significant cytotoxicity issues due to the leaching of the decomposition byproducts. Further modifications to eliminate these problems often result in other structural inadequacies that render them unsuitable for clinical applications. To overcome these fundamental limitations, NO materials are needed that (1) produce significantly high levels of NO for long periods of time and (2) allow systematic modification while maintaining the structural properties that make them suitable for clinical applications.

There is a great need for a truly biocompatible material that minimizes biofouling and other deleterious side effects and simultaneously increases the lifetime of the medical device in a safe and efficacious manner. The result of such a material would decrease healthcare costs, improve the quality of care for patients, and decrease the time physicians spend repeating procedures.

In addition, there is a need for effective methods for using the material to treat clinically relevant disorders which this disclosure encompasses. Finally, a need exists to develop the coating method that allows for applying the material in a range of thicknesses or as encapsulated particles to broaden the utility of the material as outlined in this disclosure.

SUMMARY OF THE INVENTION

Disclosed herein is a modular biomaterial that accomplishes the properties mentioned above. Specifically, the approach focuses on the utilization of nitric oxide (NO) as a therapeutic agent capable of concurrently achieving many of the aims of an ideal physiological fluid-contacting material. Nitric oxide has been shown to regulate cell responses via biochemical, structural, and physical mechanisms. Among the naturally occurring compounds that could possibly be employed as a therapeutic agent, nitric oxide has been shown to simultaneously decrease platelet adhesion and aggregation (thrombosis), decrease smooth muscle cell migration and proliferation (intimal hyperplasia), and reduce infection and inflammation. Thus, due to its ability to singularly invoke multiple desirable therapeutic responses, NO is a broadly applicable molecule for the treatment of disease states.

The present disclosure describes compounds comprised of a metal bound to organic linkers that are capable of overcoming biofouling or treating diseases, for example, but not limited to, by producing NO.

The present disclosure describes the combination of metal organic compounds with and without secondary therapeutic agents that are capable of overcoming biofouling or treating diseases.

The present disclosure describes compositions of compounds comprised of metals bound to organic linkers combined with another material or matrix such as a polymer.

The present disclosure describes a number of methods of making the subject compositions.

The present disclosure describes the use of these materials for the treatment of clinically relevant diseases or complications.

The present disclosure describes the use of these materials as coatings and material compositions for fabricating medical devices.

In one aspect the disclosure provides a method of producing nitric oxide comprising (i) providing a composition comprising a metal-organic framework, and (ii) exposing the composition to a nitric oxide-releasing compound to produce nitric oxide. In various embodiments, the aforementioned method is provided wherein the metal-organic framework has a repeating structure in 1-dimension, 2-dimensions, 3-dimensions, or a mixture thereof. In various embodiments, an aforementioned method is provided wherein the metal-organic framework comprises a polydentate organic linker.

In various embodiments an aforementioned method is provided wherein the metal-organic framework comprises a polydentate organic linker having a formula I, II, III, IV, or V;

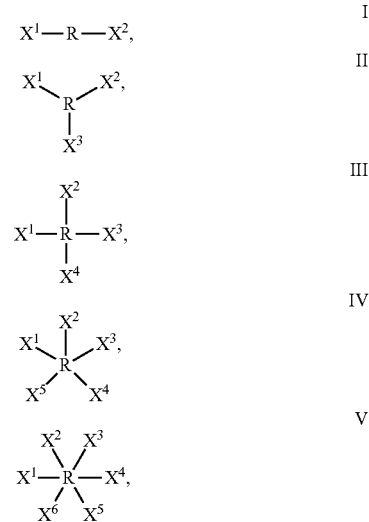

wherein $X^1$, $X^3$, $X^4$, $X^5$, and $X^6$ are each independently selected from the group consisting of $NH_2$, $CO_2H$, $SH$, nitrogen-containing heteroaromatic compounds, and nitrogen-containing heterocycles; $X^3$ is selected from the group consisting of $NH_2$, $CO_2H$, $SH$, nitrogen-containing heteroaromatic compounds, nitrogen-containing heterocycles, $C(=O)NHR'$, $C(=O)OR'$, $C(=O)SR'$, $N(H)C(=O)R'$, $OC(=O)R'$, and $SC(=O)R'$; R is selected from the group consisting of aromatic compounds, heteroaromatic compounds, cycloalkanes, and heterocycles, and R' is a therapeutic agent having one or more functional groups selected from the group consisting of $NH_2$, $OH_2$, $SH$, $C(=O)NH_2$, $C(=O)OH$, and $C(=O)SH$.

In various embodiments an aforementioned method is provided wherein the metal-organic framework comprises a polydentate organic linker having a formula XXIV; $R^8—X^7$ XXIV; wherein $X^1$ is selected from the group consisting of H, $NH_2$, $CO_2H$, $SH$, nitrogen-containing heteroaromatic compounds, nitrogen-containing heterocycles, $C(=O)NHR'$, $C(=O)OR'$, $C(=O)SW$, $N(H)C(=O)R^1$, $OC(=O)R'$, and $SC(=O)R'$; $R^a$ is selected from the group consisting of heteroaromatic compounds and heterocycles; and R' is a therapeutic agent having one or more functional groups selected from the group consisting of $NH_2$, $OH$, $SH$, $C(=O)NH_2$, $C(=O)OH$, and $C(=O)SH$; with the proviso that when $X^7$ is H, $R^a$ comprises at least two heteroatoms.

In various embodiments an aforementioned method is provided wherein the metal-organic framework comprises a metal selected from the group consisting of copper, zinc, iron, cobalt, manganese, vanadium, molybdenum, tungsten, chromium, nickel, aluminum, and mixtures thereof. In various embodiments, the metal-organic framework comprises at least first and second metal atoms, and the oxidation state of the first metal atom is different from the oxidation state of the second metal atom.

In various embodiments an aforementioned method is provided wherein the metal-organic framework comprises $Cu_3$(1,3,5-benzenetricarboxylic acid)$_2$.

In various embodiments an aforementioned method is provided wherein the metal-organic framework comprises metal atoms and polydentate organic linkers. In various embodiments an aforementioned method is provided wherein the metal-organic framework comprises at least two metal atoms and at least two molecules of a polydentate organic linker. In still other embodiments, an aforementioned method is provided wherein at least 2, 3, 4, 5, 6, 7, 8, 9, 10, 11, 12, 13, 14, 15, 16, 17, 18, 19 or 20 metal items and at least 2, 3, 4, 5, 6, 7, 8, 9, 10, 11, 12, 13, 14, 15, 16, 17, 18, 19 or 20 molecules of a polydentate organic linker are provided.

In various embodiments an aforementioned method is provided wherein the metal-organic framework has a porous structure. In various embodiments, an aforementioned method is provided wherein the metal-organic framework has a porous structure comprising pores having an average size of about 5 Å to about 500 Å in diameter.

In other embodiments an aforementioned method is provided wherein the nitric oxide-releasing compound comprises a functional group selected from the group consisting of S-nitrosothiol, diazeniumdiolate, nitrate, nitrite, nitroso, and nitrosyl.

In various embodiments an aforementioned method is provided wherein the exposing step comprises contacting the composition with blood. In various embodiments an aforementioned method is provided wherein the nitric oxide-releasing compound is present in blood.

In various embodiments an aforementioned method is provided wherein the compositions disclosed herein comprise one or more therapeutic agents. In various embodiments the compositions disclosed herein comprise one or more polymers.

In various embodiments an aforementioned method is provided wherein the method further comprises administering the compositions disclosed herein in a sufficient amount to a patient in need thereof. In various embodiments an aforementioned method is provided wherein the method further comprises administering the compositions disclosed herein in a sufficient amount to a patient in need thereof to treat any number of diseases, disorders, or conditions. In various embodiments an aforementioned method is provided wherein the composition produces nitric oxide for an extended period of time.

In another aspect the disclosure provides methods for producing nitric oxide comprising providing a composition comprising a metal-organic framework, wherein the metal-organic framework is covalently attached to a nitric oxide-releasing functional group. In various embodiments an aforementioned method is provided wherein the metal-organic framework has a repeating structure in 1-dimension, 2-dimensions, 3-dimensions, or a mixture thereof. In various embodiments, an aforementioned method is provided wherein the nitric oxide-releasing functional group is selected from the group consisting of S-nitrosothiol, diazeniumdiolate, nitrate, nitrite, nitroso, and nitrosyl. In various embodiments an aforementioned method in provided wherein the metal-organic framework comprises a polydentate organic linker selected from the group consisting of

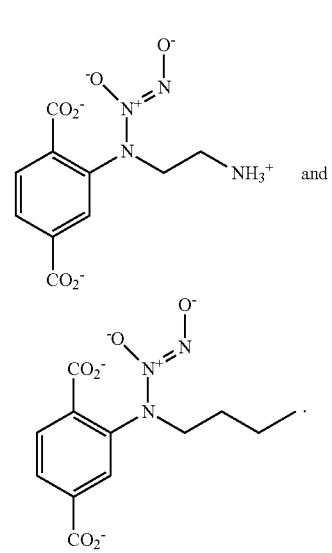

In various embodiments, an aforementioned method is provided wherein the method further comprises contacting the composition with physiological fluids or with an aqueous buffer and light. In various embodiments an aforementioned method is provided wherein the composition produces nitric oxide for an extended period of time.

In another aspect the disclosure provides nitric oxide-producing compositions comprising (i) a polymer and (ii) a metal-organic framework. In various embodiments the metal-organic framework has a repeating structure in 1-dimension, 2-dimensions, 3-dimensions, or a mixture hereof. In various embodiments, an aforementioned composition is provided wherein the metal-organic framework is covalently attached to a nitric oxide-releasing functional group. In various embodiments, an aforementioned composition is provided wherein the composition having a covalently attached nitric oxide-releasing functional group produces nitric oxide when contacted with physiological fluids or with an aqueous buffer and light. In various other embodiments an aforementioned composition is provided wherein the composition produces nitric oxide when exposed to a nitric oxide-releasing compound. In various embodiments an aforementioned composition is provided wherein the composition produces nitric oxide for an extended period of time. In various embodiments an aforementioned composition is provided wherein the polymer is selected from the group consisting of polyurethane (PU), polyesters, polyethers, silicones, silicates, poly(vinyl chloride) (PVC), acrylates, methacylates, dextran, synthetic rubber (cis-polyisoprene), polyvinyl acetate, Bakelite, polyoxybenzymethylenglyolanhydride (BAKELITE™) polychloroprene (neoprene), nylon, polystyrene, polyethylene, polypropylene, polyacrylonitrile, polyvinyl butyral (PVB), poly(vinylidene chloride), fluorinated polymers, polytetrafluoroethylene (PTFE), and mixtures and copolymers thereof. In various embodiments an aforementioned composition is provided wherein the nitric oxide-releasing functional group is selected from the group consisting of S-nitrosothiol, diazeniumdiolate, nitrate, nitrite, nitroso, and nitrosyl. In various embodiments an aforementioned composition is provided wherein the nitric oxide-releasing compound comprises a functional group selected from the group consisting of S-nitrosothiol diazeniumdiolate, nitrate, nitrite, nitroso, and nitrosyl.

In another aspect the disclosure provides nitric oxide-producing coatings comprising (i) a polymer and (ii) a metal-organic framework. In various embodiments the metal-organic framework has a repeating structure in 1-dimension, 2-dimensions, 3-dimensions, or a mixture thereof. In various embodiments an aforementioned coating is provided wherein the metal-organic framework is covalently attached to a nitric oxide-releasing functional group. In various embodiments an aforementioned coating is provided wherein the coating comprising a metal-organic framework having a covalently attached nitric oxide-releasing functional group produces nitric oxide when contacted with physiological fluids or with an aqueous buffer and light. In various other embodiments an aforementioned coating is provided wherein the coating produces nitric oxide when exposed to a nitric oxide-releasing compound. In various embodiments an aforementioned coating is provided wherein the coating produces nitric oxide for an extended period of time. In various embodiments an aforementioned coating is provided wherein the polymer is selected from the group consisting of polyurethane (PU), polyesters, polyethers, silicones, silicates, poly(vinyl, chloride) (PVC), acrylates, methacylates, dextran, synthetic rubber (cis-polyisoprene), polyvinyl acetate, Bakelite, polyoxybenzymethylenglyolanhydride (BAKELITE™) polychloroprene (neoprene), nylon, polystyrene, polyethylene, polypropylene, polyacrylonitrile, polyvinyl butyral (PVB), poly(vinylidene chloride), fluorinated polymers, polytetrafluoroethylene (PTFE), and mixtures and copolymers thereof. In various embodiments the nitric oxide-releasing functional group is selected from the group consisting of S-nitrosothiol, diazeniumdiolate, nitrate, nitrite, nitroso, and nitrosyl. In various embodiments an aforementioned coating is provided wherein the nitric oxide-releasing compound comprises a functional group selected from the group consisting of S-nitrosothiol, diazeniumdiolate, nitrate, nitrite, nitrosos, and nitrosyl.

In another aspect the disclosure provides medical devices comprising a nitric oxide-producing coating comprising (i) a polymer and (ii) a metal-organic framework. In various embodiments the metal-organic framework has a repeating structure in 1-dimension, 2-dimensions, 3-dimensions, or a mixture thereof. In various embodiments an aforementioned medical device is provided wherein the metal-organic framework is covalently attached to a nitric oxide-releasing functional group. In various embodiments an aforementioned medical device is provided wherein the medical device comprises a metal-organic framework having a covalently attached nitric oxide-releasing functional group produces nitric oxide when contacted with physiological fluids or with an aqueous buffer and light. In various other embodiments an aforementioned medical device is provided wherein the medical device produces nitric oxide when exposed to a nitric oxide-releasing compound. In various embodiments an aforementioned medical device is provided wherein the medical device produces nitric oxide for an extended period of time. In various embodiments an aforementioned medical device is provided wherein the polymer is selected from the group consisting of polyurethane (PU), polyesters, polyethers, silicones, silicates, poly(vinyl chloride) (PVC), acrylates, methacylates, dextran, synthetic rubber (cis-polyisoprene), polyvinyl acetate, Bakelite, polychloroprene (neoprene), nylon, polystyrene, polyethylene, polypropylene, polyacrylonitrile, polyvinyl butyral (PVB), poly(vinylidene chloride), fluorinated polymers, polytetrafluoroethylene (PTFE), and mixtures and copolymers thereof. In various embodiments the nitric oxide-releasing functional group is selected from the group consisting of S-nitrosothiol, diazeniumdiolate, nitrate, nitrite, nitroso, and nitrosyl. In various embodiments an aforementioned medical device is provided wherein the nitric oxide-releasing compound comprises a functional group selected from the group consisting of S-nitrosothiol, diazeniumdiolate, nitrate, nitrite, nitroso, and nitrosyl.

DETAILED DESCRIPTION

Currently, the majority of nitric oxide-releasing materials that have been reported release NO in less than 1 week. Since many clinical devices are implanted for longer than this or even permanently, there is a need to produce NO at higher levels and for these longer time frames, for either the desired lifetime of the device or until the device is incorporated naturally into the body. Further, depending on the disease state or use, the levels of NO may be varied (i.e., the amount of NO needed to promote wound healing may be longer than that needed to prevent platelet activation and adhesion). As such modular NO materials that can be made that can both have higher storage and delivery capabilities and also produce NO for longer periods of time (i.e., >1 month and preferably for the length of the implanted material) would be of a great advantage.

In order to fulfill the shortcomings described herein, this disclosure describes biocompatible compounds, compositions, methods, and uses suitable for use on or with medical devices for use with vertebrate animals. Compounds are presented that have the ability to produce nitric oxide. Compositions are described that comprise a material containing the metal-organic compounds. In various embodiments, a composition includes metal-organic compounds with other secondary therapeutic agents.

Figure 1:
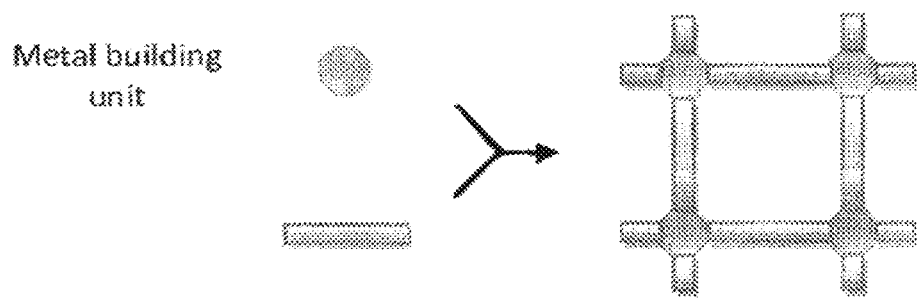
FIG. 1 is a schematic drawing depicting the modular construction of metal-organic compounds.

This disclosure describes compounds that are assembled from an organic linker and a metal building unit that can be systematically altered to produce structures of differing types (FIG. 1). By way of example and without limitation, these structures are the metal-organic frameworks known as MOF materials. The resulting materials made by combining metals and these organic linkers are, in various embodiments, 1-dimensional, 2-dimensional, and 3-dimensional structures with well-defined and repeated structural characteristics throughout the material. These materials may be extended networks or discrete, molecular polyhedron. These structures may contain a wide range of organic linkers and metal types as described herein. The structural nature of these compounds often leads to porosity that permits the inclusion of guest molecules within the pores and open spaces of the materials. These guest molecules may undergo a number of useful behaviors including (1) being passively stored, (2) chemically reacting directly with the host structure to form new bonds, and/or (3) reacting with other guest molecules in stoichiometric or catalytic reactions. In these situations, the host-guest processes can be carried out without altering the structural integrity of the host compound itself and are, therefore, very stable platforms for designing application-driven substrates. Owing to their modular nature, these materials can be tailored to have various structural shapes, chemical functionalities, pore sizes, and chemical and physical properties to match many biomedical applications.

Figure 2:
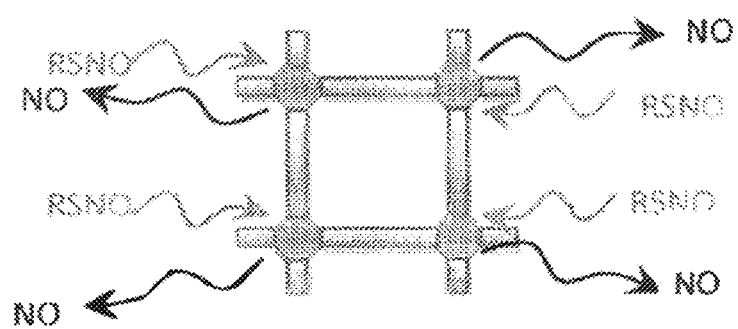
FIG. 2 is a schematic drawing depleting S-nitrosothiols reacting with metal-organic compounds to produce nitric oxide.
Figure 3A:
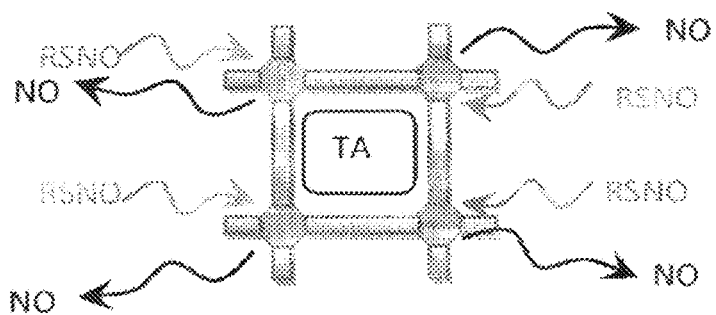
FIG. 3a is a schematic drawing depicting S-nitrosothiols reacting with metal-organic compounds to produce nitric oxide, wherein a secondary therapeutic agent (TA) is present in the pores of the metal-organic structure.
Figure 3B:
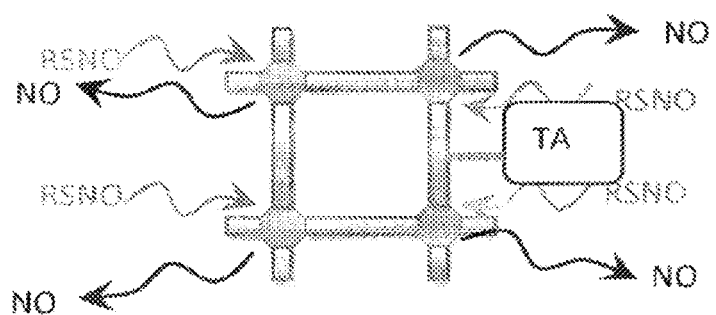
FIG. 3b is a schematic drawing depicting S-nitrosothiols reacting with metal-organic compounds to produce nitric oxide, wherein a secondary therapeutic agent (TA) is bound to the metal-organic structure.

In some embodiments, the compound may be created from a metal, a secondary building unit, or several secondary building units that may or may not be the same. The resulting 1, 2, or 3 dimensional structures produce NO from S-nitrosothiols or other NO carriers within the fluid when exposed to physiological fluids such as shown, by way of example, in FIG. 2. These structures can be used in polymer films alone or with additional therapeutic agents as shown in FIGS. 3A and 3B.

Figure 4:
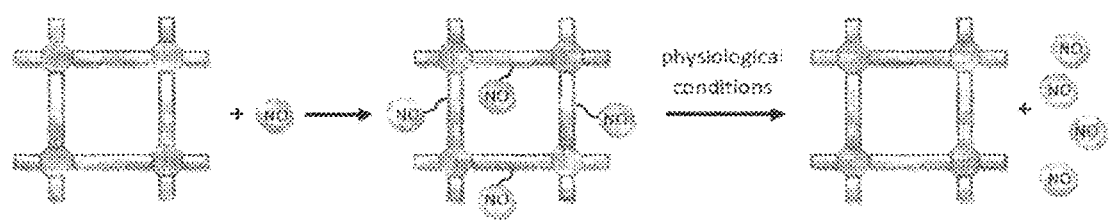
FIG. 4 is a schematic drawing depicting the structural rigidity and improved nitric oxide delivery capabilities of metal-organic compounds.

The modular nature of the metal organic compound structures allow NO functionalities to be incorporated directly and covalently onto the structure of the material substrate. Structures can be formed with the same structural topology but different chemical functions in the backbone linker (referred to as isoreticular chemistry). The ability to systematically modify the organic linker for use with a variety of functional moieties allows NO-releasing metal-organic compounds to be prepared (see FIG. 4). Ingleson, Heck, Gould, and Rosseinsky (*Inorg. Chem.*, 48:9986-9988, 2009) reported one such compound. In various embodiments, the metal-organic compound may be selected from a metal, a secondary building unit, or several secondary building units that may or may not be the same. The linkers in the secondary building units may contain covalently attached NO-releasing moiety including, but not limited to, NO prodrugs. The metal-organic compounds can have a range of stereochemistries. The organic linker and metal may be chosen in combinations to create controlled and specific stereochemistry. Primary nitric oxide therapeutic agents can be contained in the metal-organic structure either as bound to the linkers or non-specifically contained within the open spaces of the host structure (see FIG. 3B). Secondary therapeutic agents may also be combined into the structure.

As an example, diazeniumdiolate and S-nitrosothiol are formed on nitrogen and sulfur-based functional groups. The organic linkers used to create the metal-organic structures can be readily modified to incorporate the necessary nitrogen and sulfur based linkers required to allow the metal-organic structures to be generated that can store and release NO in blood-contacting systems. Reaction of these linkers with either pure NO gas or acidified sodium nitrite would then form diazeniumdiolate and S-nitrosothiol functions directly on the metal-organic compound. Under physiological conditions, these two NO-donor functions will directly release NO from the material into the local environment and result in the desired clinical response.

Figure 5:
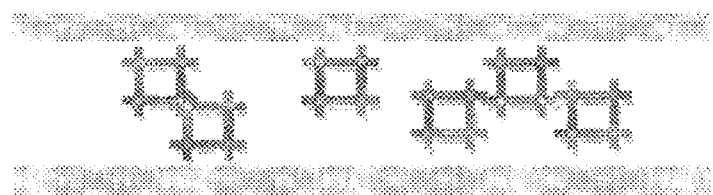
FIG. 5 is a schematic drawing depicting a material containing metal-organic compounds.

These compounds when incorporated into polymers can produce NO, rendering a material that can deliver therapeutic agents, such as nitric oxide locally as shown in FIG. 5. The therapeutic agents can be incorporated into a single material or into any layers of a multi-component configuration. If multiple therapeutic agents are used, the therapeutic agents can be in the same material layer or different material layers. Not all of the material layers used need to have a therapeutic agent. Each layer of the overall material may contain a unique combination of zero, one, or multiple therapeutic components.

While others have demonstrated the synthesis of specific porous compounds (see, U.S. Pat. No. 5,648,508) and metal complexes that can generate NO from endogenous blood containing species (see, U.S. Pat. Nos. 7,128,904, 7,335,383, 7,763,283, US 2008/0226686, and US 2009/0118819), the present disclosure overcomes limitations of the current state of the art compounds in several ways. The modular structures of nitric oxide metal-organic materials make them stand out in remarkable contrast to current nitric oxide materials and present a significant departure and innovation over the current state-of-the-art capabilities in biomaterials. The materials combine the modular and structural stability of metal-organic compounds with the therapeutic action of NO-production in a controlled delivery fashion to create NO-releasing metal-organic compounds. The innovation of the approach lies in coupling the two divergent research fields in ways that takes full advantage of the benefits of each field: (1) the use of modular metal-organic compounds in biological applications and (2) the use of NO donor and catalysis chemistries in a single compound that can be used universally in a wide range of medical devices. The combination of these two areas allow the clinical efficacy of NO to be finely modulated in order to deliver precisely-desired amounts of NO in any given medical application. Specifically, the NO biomaterials disclosed herein are a significant enhancement compared to other NO materials for at least the following reasons:

First, the materials provide unprecedented control over the kinetic profile and biological functions of NO materials. Three factors allow nitric oxide metal-organic materials to be quickly and routinely altered to tailor the kinetic and biological factors: (1) modular control over the topology by choice of metal and organic linker combination, (2) the ability to alter the chemical and structural features of the organic linker, and (3) the ability to create hybrid and composite materials by blending with organic polymers.

Second, since the metal-organic compound is ordered and has a controlled and fixed amount of reactive sites. It has the potential to produce significantly more NO groups than current biomedical polymers. For example, the typical NO polymer material may have 0.3 mmol NO groups/gram of polymer whereas nitric oxide metal organic compounds will to load 100 times that amount per gram of substrate. As a result, the limitation on NO storage in current materials would be overcome by several orders of magnitude or more.

Third, the necessary mechanical properties of current NO polymers often are lost when NO substrates are introduced to the organic polymer. Due to the structural features of the metal-organic compounds described herein, the materials will retain their mechanical properties and not suffer from the degradation that is inherent in current nitric oxide materials. This is especially important since leaching and cytotoxicity issues are often a direct result of NO material decomposition and structures that remain intact and active are necessary and desirable for biomedical applications.

Fourth, metal-organic compounds have metal sites that can serve as catalytic sites to produce NO from physiological fluid components. Because these metals are integrated into the repeating structure of the metal-organic and are accessible within the structure, there are a large number of conversion sites that can be easily accessed by endogenous NO carriers. This is in contrast to currently used flexible polymer systems where polymer folding often slows and/or prevents small molecules from diffusing from the plasma and into available catalytic sites. The availability of metal sites in the metal-organic compounds described herein provide the ability to produce low levels of NO for extended periods of time in order to maintain the biocompatibility of the material beyond the initial high levels of NO release.

Fifth, due to their structural features, metal-organic materials are easily blended into typical organic polymers such as, but not limited to, polyurethanes and poly(vinyl chloride). When blended, the metal-organic compound structure allows the NO functionalities and the metal sites to remain accessible for biological function. Thus, these materials are readily integrated with and applied to a range of medical applications. In addition, the blending or layering of these materials allows additional control over the release levels of NO achieved from these materials.

Thus, in one embodiment, the metal-organic materials are incorporated into another material, such as a polymer. In various embodiments, the material can be a polymer that has additional chemical functionalities such as, but not limited to, amine, carboxyl, halide, ketone, urethane, urea, silicone, or aldehyde groups. The material also has differing degrees of porosity or diffusion characteristics.

Other embodiments of the disclosure include encapsulating the metal-organic compounds into other materials such as polymers.

In still another embodiment, compositions include adding a secondary therapeutic agent to the material in concert with the metal-organic compound that produces nitric oxide. The secondary therapeutic agent could be covalently attached to the metal-organic compound, blended with the metal-organic compound, or blended into another material such as an organic polymer. The secondary therapeutic agent may also be covalently attached to the metal-organic compound or non-specifically bound to the metal-organic compound.

I. Definitions

For convenience, before further description of the present disclosure, certain terms used in the specification and examples are described here. These definitions should be read in light of the remainder of the disclosure and understood as by a person of skill in the art. Also, the terms "including" (and variants thereof), "such as", "e.g.", "i.e." as used herein are nonlimiting and are for illustrative purposes only.

The articles "a" and "an" are used herein to refer to one or to more than one (i.e, to at least one) of the grammatical object of the article. By way of example, "an element" means one element or more than one element.

"Metal organic compound" consists of linkers coordinated to metals resulting in a 1-dimensional, 2-dimensional, or 3-dimensional structure with well-defined and repeated structural characteristics throughout the material.

"Linker" Is a multidentate ligand that binds to metals through coordinate covalent bonds such that it acts as a connector between geometric centers.

"Secondary building unit" is a metal or multiple metals coordinated to organic linkers or other ligand molecules that act as a geometric center for a metal-organic structure.

"Frameworks" are commonly used to refer to extended networks although the term may also refer to discrete polyhedral structures, still consisting of a metal and an organic linker. Examples of these include, but are not limited to, metal-organic frameworks (MOF) and metal-organic polyhedra (MOP). Metal organic frameworks include compounds having translational symmetry in 1-dimension, 2-dimensions, 3-dimensions, or a mixture thereof. Metal organic frameworks include compounds having an extended network structure, for example, compounds comprising repeating structures such as linear structures, rods, triangles, squares, tetrahedral structures, trigonal bipyramidal structures and octandedral structures. The metal organic frameworks include compounds having one repeating structure or more than one repeating structures, for example, two, three, four, or more different repeating structures. Of course, one of skill in the art would understand that MOFs are extended networks where size is determined by the crystal dimensions. For example, one MOF may have on the order of $10^{17}$ atoms in one extended structure.

"Host-guest" is a term that describes the relationship between a discrete compound ("guest") that is located within the pores or open spaces of a metal-organic compound ("host"). The discrete guest and the metal-organic compound in this relationship are not strongly covalently bonded. In many cases, the discrete guest compound, such as carbon dioxide gas, is stored in the pores and open spaces of the host, such as MOF compounds typically exhibit.

"Porosity" describes the sum of the void spaces in a material. The higher the void space compared to material space, the higher the porosity. Porosity can range from 0 to 100%.

"Catalysis" refers to the process in which the rate of a chemical reaction is increased by adding an additional chemical compound. In the process, the added chemical compound is not consumed by the reaction. The process usually occurs, but is not limited to, by lowering the activation energy required to promote the forward rate of the reaction. It may also promote increased rates by preorganization or physical arrangement of the reaction components making increased reaction rates more probable.

As used herein, "secondary therapeutic agent" refers to compounds that cause a desirable and beneficial physiological result in response to the compound. Exemplary compounds are described herein.

"Material" and "matrix" refer to the material that metal-organic compounds, therapeutic agents, and secondary therapeutic agents are contained within. These can include, but are not limited to, plastics, cements, and clays.

"Polymer" is a large molecule composed of repeating structural or constitutional units, usually referred to as monomers, connected by covalent chemical bonds. Polymers can consist of the same or differing repeat units in order or random fashion. Polymers may take on a number of configurations, which may be selected, for example, from cyclic, linear, branched and networked (e.g., crosslinked) configurations. Branched configurations include star-shaped configurations (e.g., configurations in which three or more chains emanate from a single branch point, such as a seed molecule), comb configurations (e.g., configurations having a main chain and a plurality of side chains), dendritic configurations (e.g., arborescent and hyperbranched polymers), and so forth. As used herein, "homopolymers" are polymers that contain multiple copies of a single constitutional unit. "Copolymers" are polymers that contain multiple copies of at least two dissimilar constitutional units, examples of which include random, statistical, gradient, periodic (e.g., alternating), and block copolymers.

"Plasticizer" is art recognized, and includes a compound that is added to polymers that increases the plasticity or fluidity of the material to which they are added. Some examples include, but are not limited to, dicarboxylic/ tricarboxylic ester-based plasticizers such as dioctyl sebacate (DOS), benzoates, sulfonamides, organophosphates, and glycols, or benzoates.

The terms "blend", "layered", "hybrid", "composite", and "hybrid-composite" are used to describe materials that are made from more than one component and in various combinations.

"Interpenetrating network" (IPN) describes any material containing two macromolecular compounds, such as polymers or metal-organic compounds whose structures interweave and fill the spaces of the other substance by physical means. These networks may or may not have chemical interactions with each other.

"Producing" is a generic term used to describe all mechanisms of delivery including generating and releasing modes.

"Biocompatibility" is a generic term that describes an interaction or relationship with physiological or biological systems.

"Medical device" refers to product which is used for medical purposes in patients, in diagnosis, therapy, treatment, or surgery. If applied to the body, the effect of the medical device can be physical or chemical.

"Biodegradable" means chemical breakdown of materials by a physiological environment. This can include, but is not limited to physiological fluids such as blood and blood components, subcutaneous fluid, tissue fluid, or urine.

"Bioerodable" refers to the chemical breakdown of material by the physiological environment beginning at the surface of the material.

"Physiological fluid" refers to any fluid produced by the body, including but not limited to, subcutaneous fluid, saliva, blood, extracellular fluid, and urine.

"Aromatic compound" refers to a monocyclic or polycyclic ring system, preferably a monocyclic or bicyclic ring system, containing one or more aromatic rings, e.g., benzene or naphthalene. Unless otherwise indicated, an aromatic compound can be unsubstituted or substituted with one or more, and in particular one to four groups independently selected from, for example, halo, alkyl, alkenyl, —OCF$_3$, —NO$_2$, —CN, —NC, —OH, alkoxy, amino, —CO$_2$H, —CO$_2$-alkyl, aryl, and heteroaryl. Exemplary aromatic compound include, but are not limited to, benzene, naphthalene, tetrahydronaphthalene, chlorobenzene, methylbenzene, methoxybenxene, trifluorotmethylbenzene, nitrobenzene, 2,4-methoxychlorobenzene, and the like.

"Heteroaromatic compound" refers to a monocyclic or polycyclic ring system, preferably a monocyclic or bicyclic ring system, containing one or more aromatic rings and containing at least one nitrogen, oxygen, or sulfur atom in an aromatic ring. Unless otherwise indicated, a heteroaromatic compound can be unsubstituted or substituted with one or more, and in particular one to four, substituents selected from, for example, halo, alkyl, alkenyl, —OCF$_3$, —NO$_2$, —CN, —NC, —OH, alkoxy, amino, —CO$_2$H, —CO$_2$-alkyl, aryl, and heteroaryl. Examples of heteroaromatic compound include, but are not limited to, thiophene, furan, pyridine, oxazole, quinoline, thiobenzene, isoquinoline, indole, triazine, triaxole, isothlazole, isoxazole, imidazole, benzothiazole, pyrazine, pyrimidine, thiazole, and thiadiazole.

"Cycloalkane" refers to a cyclic hydrocarbon, e.g., cyclopropane, cyclobutane, cyclohexane, and cyclopentane. "Heterocycle" is defined similarly as cycloalkane, except the ring contains one or more hetereatoms independently selected from the group consisting of oxygen, nitrogen, and sulfur. Nonlimiting examples of heterocycles include piperdine, tetrahydrofuran, tetrahydropyran, dihydrofuran, and the like. Cycloalkanes and heterocycles can be saturated or partially unsaturated ring systems optionally substituted with, for example, one to three groups, independently selected from the group consisting of alkyl, alkylene-OH, —C(O)NH$_2$, —NH$_2$, —NO$_2$, oxo (=O), aryl, haloalkyl, halo, —OH and —SH. Heterocycloalkyl groups optionally can be further N-substituted with alkyl, hydroxyalkyl, alkylenearyl, or alkyleneheteroaryl.

II. Compounds

In various embodiments, compounds of the present disclosure include metal-organic compounds used with or without other therapeutic agents.

In another embodiment, the metal-organic compounds are made by several synthetic methods including base diffusion, solvothermal, or microwave.

In still another embodiment, the metal-organic compounds have linkers that are polydentate and bind to at least two or more metals. In various embodiments, the metal-organic framework comprises an polydentate organic linker selected from the group consisting of terephthalic acid, trimesic acid (i.e., 1,3,5-benzenetricarboxylic acid), pyridine-2,5-dicarboxylic acid, isophthalic acid, 2H-imidazole-4,5-dicarboxylic acid, 4,4'-bipyridine, biphenyl-4,4'-dicarboxylic acid, naphthalene-2,6-dicarboxylic acid, 4,4',4"-(1,3,5-triazine-2,4,6-triyl)tribenzoic acid, pyridine-3,5-dicarboxylic acid, 4H-imidazole, 4,4',4",4"'-methanetetrabenzoic acid, 1,4-di(1H-tetrazol-5-yl)benzene, 1,3,5-tri(1H-tetrazol-5-yl)benzene, 1,3,5-tri(1H-1,2,3-triazol-4-yl)benzene, 4,4',4"-methanetriyltribenzoic acid, pyrazine-2,3-dicarboxylic acid, 4,4',4"-nitrilotribenzoic acid, and mixtures thereof.

Terephthalic Acid:

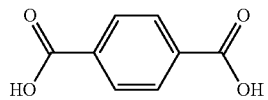

Trimesic Acid:

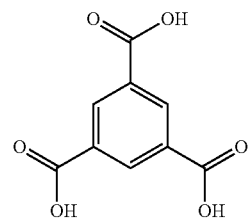 [SMILES: O=C(O)c1cc(C(=O)O)cc(C(=O)O)c1]

In various embodiments, the polydentate linkers have the same or different chemical groups.

In various embodiments, the polydentate organic linkers have a formula I, II, III, IV, or V:

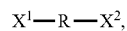

I

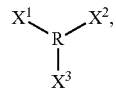

II

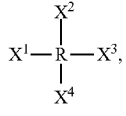

III

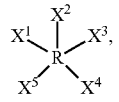

IV

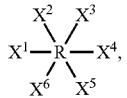

V wherein $X^1$, $X^2$, $X^4$, $X^5$, and $X^6$ are each independently selected from the group-consisting of $NH_2$, $CO_2H$, SH, nitrogen-containing heterearomatic compounds, and nitrogen-containing heterocycles; $X^3$ is selected from the group consisting of $NH_2$, $CO_2H$, SH, nitrogen-containing heteroaromatic compounds, nitrogen-containing heterocycles. C(=O)NHR', C(=O)OR', C(=O)SR', N(H)C(=O)R', OC(=O)R', and SC(=O)R'; R is selected from the group consisting of aromatic compounds, heteroaromatic compounds, cycloalkanes, and heterocycles, and R' is a therapeutic agent having one or more functional groups selected from the group consisting of $NH_2$, OH, SH, C(=O)$NH_2$, C(=O)OH, and C(=O)SH.

In some embodiments, the nitrogen-containing heteroaromatic compound is selected from the group consisting of pyrrolyl (e.g., pyrrol-2-yl, pyrrol-3-yl), imidazolyl (e.g., imidazol-2-yl, imidazol-4-yl, imidazol-5-yl), pyrazolyl (e.g., pyrazol-3-yl, pyrazol-4-yl, pyrazol-5-yl), oxazolyl (e.g., oxazol-2-yl, oxazol-4-yl, oxazol-5-yl), isoxazolyl (e.g., isoxazol-3-yl, isoxazol-4-yl, isoxazol-5-yl), thiazolyl (e.g., thiazol-2-yl, thiazol-4-yl, thiazol-5-yl), isothiazolyl, (e.g., isothiazol-3-yl, isothiazol-4-yl, isothiazol-5-yl), triazolyl (e.g., 1,2,3-triazol-4-yl, 1,2,3-triazol-5-yl, 1,2,4-triazol-3-yl, 1,2,4-triazol-5-yl), oxadiazolyl (e.g., 1,2,5-oxadiazol-3-yl, 1,2,5-oxadiazol-4-yl), tetrazolyl (e.g., tetrazol-5-yl), pyridinyl (e.g., pyridin-2-yl, pyridin-3-yl, pyridin-4-yl), pyrazinyl (e.g., pyrazin-2-yl), pyrimidinyl (e.g., pyrimidin-2-yl, pyrimidin-4-yl, pyrimidin-5-yl), pyridazinyl (e.g., pyridazin-3-yl, pyridazin-4-yl), triazinyl (e.g., 1,2,3-triazin-4-yl, 1,2,3-triazin-5-yl, 1,2,4-triazin-3-yl, 1,2,4-triazin-5-yl, 1,2,4-triazin-6-yl, 1,3,5-triazin-2-yl), and tetrazinyl (e.g., 1,2,3,4-tetrazin-5-yl, 1,2,4,5-tetrazin-3-yl).

In some embodiments, the nitrogen-containing heterocycle is selected from the group consisting of pyrrolidinyl (e.g., pyrrolidin-2-yl, pyrrolidin-3-yl), imidazolinyl (e.g., imidazolin-2-yl, imidazolin-4-yl, imidazolin-5-yl), imidazolidinyl (e.g., imidazolidin-2-yl, imidazolidin-4-yl), pyrazolidinyl (e.g., pyrazolidin-3-yl, pyrazolidin-4-yl), oxazdlidinyl (e.g., oxazolidin-2-yl, oxazolidin-4-yl, oxazolidin-5-yl), oxazolinyl (e.g., oxazolin-2-yl, oxazolin-4-yl, oxazolin-5-yl), thiazohdinyl (e.g., thiazolidin-2-yl, thiazolidin-4-yl, thiazolidin-5-yl), thiazolinyl (e.g., thiazolin-2-yl, thiazolin-4-yl, thiazolin-5-yl), dithiazolyl (e.g., 1,4,2-dithiazol-3-yl, 1,4,2-dithiazol-5-yl), piperidinyl (e.g., piperidin-2-yl, piperidin-3-yl, piperidin-4-yl), piperazinyl (e.g., piperazin-2-yl), morpholinyl (e.g., morpholin-2-yl, morpholin-3-yl), and thiazinyl (e.g., thiazin-2-yl, thiazin-3-yl).

In some embodiments R is selected from the group consisting of cyclopentane, cyclohexane, cycloheptane, cyclooctane, and adamantane. In some embodiments R is selected from the group consisting of benzene, naphthalene, phenanthrene, 1.5a'-dihydropene, 1,1'-biphenyl, 1,1':4',1''-terphenyl, 5'-phenyl-1,1':3',1''-terphenyl, catechol, pyrazine, pyridine, 2,2'-bipyridine, 3,3'-bipyridine, 4,4'-bipyridine, and 1,3,5-tri(pyridin-4-yl)benzene.

In various embodiments, the polydentate organic linker has a formula VI, VII, VIII, IX, X, XI, or XII:

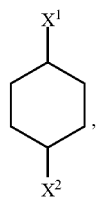

VI

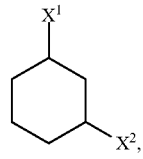

VII

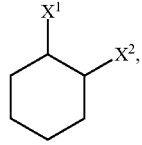

VIII

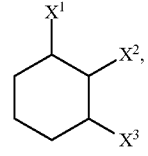

IX

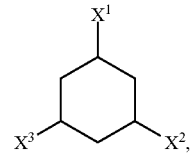

X

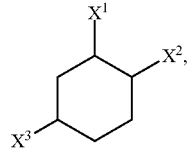

XI

-continued

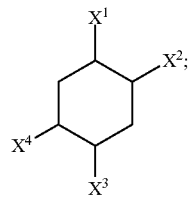
XII wherein $X^1$, $X^2$, $X^3$, and $X^4$ are defined herein. In various embodiments, the polydentate organic linker has a formula XIII or XIV:

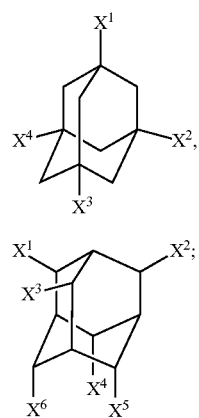
XIII

XIV wherein $X^1$, $X^2$, $X^3$, $X^4$, $X^1$, and $X^6$ are defined herein.

In various embodiments, the polydentate organic linker has a formula XV:

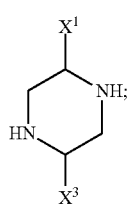
XV wherein $X^1$ and $X^3$ are defined herein.

In various embodiments, the polydentate organic linker has a formula XVI, XVII, XVIII, XIX, Xx, or XXi:

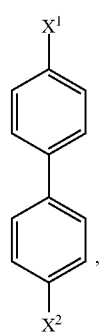
XVI

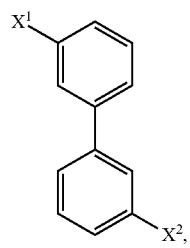
XVII

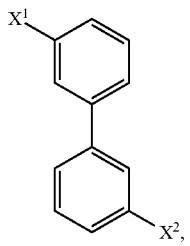
XVIII

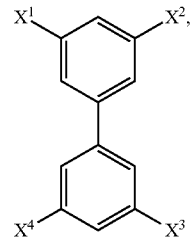
XIX

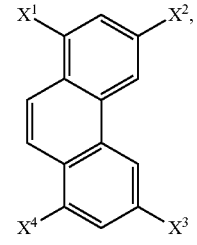
XX

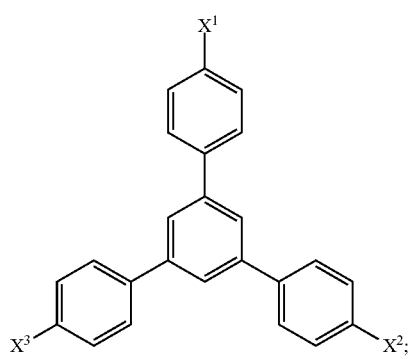
XXI wherein $X^1$, $X^2$, $X^3$, and $X^4$ are defined herein.

In various embodiments, the polydentate organic linker has a formula XXII or XXIII:

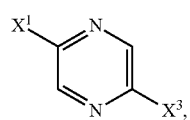
XXII

-continued

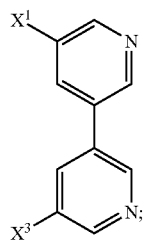

XXIII wherein $X^1$ and $X^3$ are defined herein.

In various embodiments, the polydentate organic linkers have a formula XXIV: $R^a$—$X^7$ XXIV; wherein $X^7$ is selected from the group consisting of H, $NH_2$, $CO_2H$, SH, nitrogen-containing heteroaromatic compounds, nitrogen-containing heterocycles, C(=O)NHR', C(=O)OR', C(=O)SR', N(H)C(=O)R', OC(=O)R', and SC(=O)R'; $R^a$ is selected from the group consisting of heteroaromatic compounds and heterocycles; and R' is a therapeutic agent having one or more functional groups selected from the group consisting of $NH_2$, OH, SH, C(=O)$NH_2$, C(=O)OH, and C(=O)SH; with the proviso that when $X^7$ is H, $R^a$ comprises at least two heteroatoms.

In various embodiments, the polydentate organic linkers have a formula XXV:

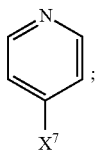

XXV wherein $X^7$ is defined herein. In various embodiments the polydentate organic linker is selected from the group consisting of pyrazine, pyridine, 2,2'-bipyridine, 3,3'-bipyridine, 4,4'-bipyridine, and 1,3,5-tri(pyridin-4-yl)benzene.

The metal-organic compounds contain metals particularly biologically significant metals such as, but not limited to, copper, zinc, iron, cobalt, manganese, vanadium, molybdenum, tungsten, chromium, nickel, and aluminum.

The metal-organic compounds contain metals that can either maintain their oxidation state within the metal-organic compound or change oxidation states within the metal-organic compound. Compounds of the same metal may contain metals with different oxidation states. For example, a combination of Fe(II) and Fe(III) could be combined with an organic linker to produce a mixed-valence metal-organic compound.

The metal-organic compounds contain secondary building units made from one or more metal atoms combined to the organic linkers. In some embodiments, the secondary building units have a geometry that is different from the overall geometry of the metal-organic framework. For example, a 'paddlewheel' motif can involve simultaneous binding of the same linker function to two separate metals to form one larger geometric unit.

Paddlewheel Binding:

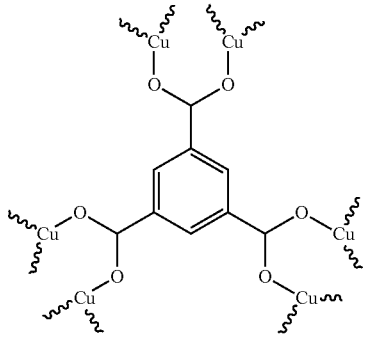

Figure 9:
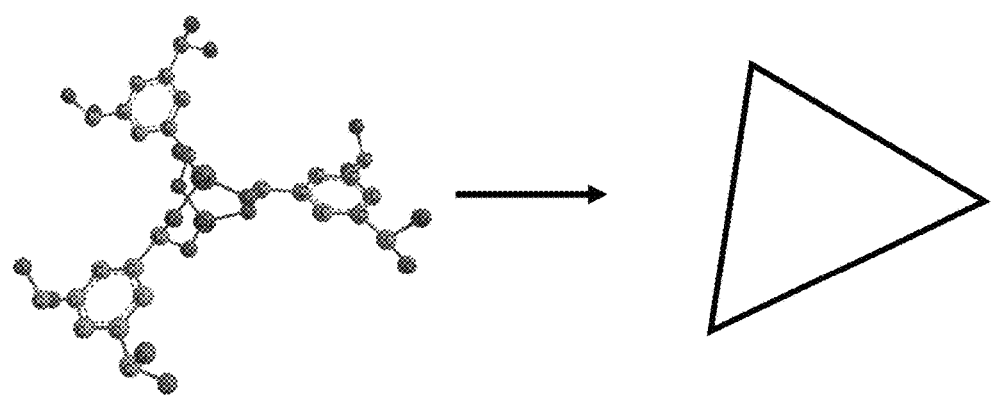
FIG. 9 is a schematic illustrating a paddlewheel building unit forming a triangular building unit.

The metal-organic compounds contain secondary building units that act as geometric centers or structural nodes. For example, the paddlewheel building unit can form a triangular building unit as illustrated in FIG. 9.

In some embodiments, the metal-organic framework has a porous structure. In some embodiments, the porous structure of the metal-organic framework comprises pores having an average size of up to 500 Å in diameter, for example, about 5 Å to about 500 Å, about 10 Å to about 200 Å, about 15 Å to about 100 Å, and/or about 20 Å to about 50 Å.

In still another embodiment, the metal-organic compounds undergo postsynthetic modification so that they can be functionalized with other chemical moieties after they are formed. In various embodiments, the metal-organic compounds have one or more of the following properties:

The metal-organic compounds have various stereochemistries and can form both symmetric and asymmetric structures;

The metal-organic compounds form 1-dimensional, 2-dimensional, and 3-dimensional extended or polyhedral structures that have a range of channel shapes, porosities, sizes, and rigidities;

The metal-organic compounds can be rigid or "breath" to alter open space and pore/channel dimensions;

The metal-organic compounds can be permeable to gases and may be selective to gases and other compounds based on structural or chemical properties;

The metal-organic compounds can be catalytic. For example, Cu-BTC (1,3,5-benzene tricarboxylate) has open metal sites in the metal-organic compound; these metal positions can act as catalytic centers allowing other reactions to take place at the open coordination sites;

The metal-organic compounds can have host-guest interactions. For example, nitric oxide can have weak intermolecular interactions with the surface of the metal-organic structure; and/or The metal-organic compounds have nitric oxide releasing, moieties such as S-nitrosothiols, diazeniumdiolates, nitrates such as glyceryl trinitrate (GTN), nitrites, nitroso, NO aspirin, and nitrosyls covalently bound to the organic linkers.

III. Therapeutic Agents

The therapeutic agents or secondary therapeutic agents consist, in one embodiment, of pharmaceutically active compounds that are covalently bound to the organic linker in the metal-organic compound. In another embodiment, the therapeutic agents consist of pharmaceutically active compounds that are non-specifically found within the open spaces of the metal-organic compound. In still another embodiment, the therapeutic agents consist of pharmaceutically active compounds that are contained with the matrix material and are not associated with the metal-organic compound.

Exemplary non-genetic therapeutic agents for use in conjunction with the present disclosure include but are not limited to: (a) anti-thrombotic agents such as heparin, heparin derivatives, urokinase, and PPack (dextrophenylalanine proline arginine chloromethylketone); (b) anti-inflammatory agents such as dexamethasone, prednisolone, corticosterone, budesonide, estrogen, sulfasalazine and mesalamine; (e) antineoplastic/antiproliferative/anti-miotic agents such as paclitaxel, 5-fluorouracil, cisplatin, vinblastine, vincristine, epothilones, endostatin, angiostatin, angiopeptin, monoclonal antibodies capable of blocking smooth muscle cell proliferation, and thymidine kinase inhibitors; (d) anesthetic agents such as lidocaine, bupivacaine and ropivacaine; (e) anti-coagulants such as D-Phe-Pro-Arg chloromethyl ketone, an RGD peptide-containing compound, heparin, hirudin, antithrombin compounds, platelet receptor antagonists, anti-thrombin antibodies, antiplatelet receptor antibodies, aspirin, prostaglandin inhibitors, platelet inhibitors and tick antiplatelet peptides; (f) vascular cell growth promoters such as growth factors, transcriptional activators, and translational promoters; (g) vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; (h) protein kinase and tyrosine kinase inhibitors (e.g., tyrphostins, genistein, quinoxalines); (i) prostacyclin analogs; (j) cholesterol-lowering agents; (k) angiopoietins; (I) antimicrobial agents such as triclosan, cephalosporins, aminoglycosides and nitrofurantoin; (m) cytotoxic agents, cytostatic agents and cell proliferation affectors; (n) vasodilating agents; (o) agents that interfere with endogenous vasoactive mechanisms; (p) inhibitors of leukocyte recruitment, such as monoclonal antibodies; (q) cytokines; (r) hormones; (s) inhibitors of HSP 90 protein (i.e., Heat Shock Protein, which is a molecular chaperone or housekeeping protein and is needed for the stability and function of other client proteins/signal transduction proteins responsible for growth and survival of cells) including geldanamycin, (t) alpha receptor antagonist (such as doxazocin, Tamsulosin) and beta receptor agonists (such as dobutamine, salmeterol), beta receptor antagonist (such as atenolol, metaprolol, butoxamine), angiotensin-II receptor antagonists (such as losartan, valsartan, irbesartan, candesartan and telmisartan), and antispasmodic drugs (such as oxybutynin chloride, flavoxate, tolterodine, hyoscyamine sulfate, diclomine), (u) bARKct inhibitors, (v) phospholamban inhibitors, (w) Serca 2 gene/protein, (x) immune response modifiers including aminoquizolines, for instance, imidazoquinolines such as resiquimod and imiquimod, and (y) human apolioproteins (e.g., AI, AII, AIII, AIV, AV, etc.). Exemplary genetic therapeutic agents for use in conjunction with the present disclosure include anti-sense DNA and RNA as well as DNA coding for the various proteins (as well as the proteins themselves): (a) anti-sense RNA, ribozymes, (b) tRNA or rRNA to replace defective or deficient endogenous molecules, (c) angiogenic and other factors including growth factors, such as acidic and basic fibroblast growth factors, vascular endothelial growth factor, endothelial mitogenic growth factors, epidermal growth factor, transforming growth factor a and R, platelet-derived endothelial growth factor, platelet-derived growth factor, tumor necrosis factor a, hepatocyte growth factor and insulin-like growth factor, (d) cell cycle inhibitors including CD inhibitors, and (e) thymidine kinase ("TKE") and other agents useful for interfering with cell proliferation. Also of interest is DNA encoding for the family of bone morphogenic proteins ("BMP's"), including BMP-2, BMP-3, BMP-4, BMP-5, BMP-6 (Vgr-1), BMP-7 (0P-1), BMP-8, BMP-9, BMP-10, BMP-11, BMP-12, BMP-13, BMP-14, BMP-15, and BMP-16. Currently preferred. BMP's are any of BMP-2, BMP-3, BMP-4, BMP-5, BMP-6 and BMP-7. These dimeric proteins can be provided, as homodimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNA's encoding them.

IV. Matrices and Polymers

The present disclosure includes one or more matrices in varying composition and combination. The matrices can consist of: (i) polymers, fibers, clays, and/or composite materials that contain the metal-organic compounds; (ii) polymers, fibers, clays, and/or composite materials that do not contain any additional compounds; (iii) polymers, fibers, clays, and/or composite materials that contain secondary therapeutic agents; and (iv) polymers, fibers, clays, and/or composite materials that contain both secondary therapeutic agents and metal-organic compounds.

By way of example, polymers include, but are not limited to, synthetic polymers such as polyurethane (PU), polyesters, polyethers, silicones, silicates, poly(vinyl chloride) (PVC), acrylates, methacylates, dextran, synthetic rubber (cis-polyisoprene), polyvinyl acetate, Bakelite, polychloroprene (neoprene), nylon, polystyrene, polyethylene, polypropylene, polyacrylonitrile, polyvinyl butyral (PVB), poly(vinylidene chloride), or fluorinated polymers such as polytetrafluoroethylene (PTFE) where either or both of the metal-organic compounds and secondary therapeutic agents are incorporated. These synthetic materials can be used as homopolymers or multi-component polymers (i.e., copolymer, tri-polymers, etc). The polymers may be hydrophobic or hydrophilic or contain regions of both hydrophobicity and hydrophilicity.

Natural polymers such as DNA, phosphodiesters, polysaccharides, or glycosides where either or both of the metal organic compounds and secondary therapeutic agents are incorporated, are also contemplated by the present disclosure.

Biodegradable or bioerodable polymers, in whole or in part, of the final material formulation, are also contemplated. Examples of biodegradable or bioerodable polymers may include, but are not limited to, polyesteramides, polyglycolide, polyanhydrides, polyorthoesters, ureas, urethanes, esters, ethers, polyhydroxybutyrate (PHB), polyhydroxyvaleratepolylactide, poly(ε-caprolactone), polyiminocarbonate, poly(dioxanone), polyarylates, as well as co-polymers of these and other monomers such as ε-caprolactone with di-lactide, ε-caprolactone with glycolide, lactide with glycolide, and glycolide with trimethylene carbonate (TMC). Amino acid based polymers such as tyrosine-derived polycarbonates are also contemplated.

The composition may also include fibrous matrices, composite materials, layering, or blends. Nano- or micro-particles of the matrix material incorporated with secondary therapeutic agents used either alone or in combination with another matrix material are included. For example, the metal-organic compounds can be encapsulated into a biodegradable cellulose material which is then delivered orally or is blended into another polymer matrix such as polyurethane and used as a permanent coating implant.

Compositions, configurations, and uses of compounds disclosed herein have the mechanical properties that match the application such that the material in its final embodiment remains sufficiently strong until the surrounding tissue has healed, does not invoke an inflammatory or toxic response, and for biodegradable application is metabolized in the body after fulfilling its purpose, leaving no trace. Further, the material is easily processed into the final product form, demonstrates acceptable shelf life, and is sterilized by acceptable methods such as ethylene oxide, gamma, or auto-clave.

Matrix materials for use in the present disclosure have various degrees of crystalline or amorphous character, ranging from 100% crystalline to 100% amorphous. Matrices are provided, according to the disclosure, with a range of differing microdomains and morpholgies that aid in the final application. The matrix materials are used according to this disclosure regardless of their stereochemistry. Both regio- and stereoisomerization forms of the matrix material can be used. For example, the present disclosure can be practiced using polymers with multiple stereochemical forms such as isostatic, syndiostatic, and atactic.

V. Methods of Preparing Compounds and Compositions

Methods of preparing compounds and compositions disclosed herein include swelling a material or a device in the presence of an organic solvent containing the appropriate metal-organic compound with or without a secondary therapeutic agent. If the metal-organic compound is incorporated into a material by swelling, then the resulting material may be coated onto a substrate or device. The methods by which the coating may be done include, hut are not limited to dip-coating, spray-coating, molding and other methods by one skilled in the art of device coatings. If the device is coated with the polymer first then swelled to incorporate the metal-organic compound then the resulting device is dried to return the coated polymer to its original dry state.

In another embodiment, methods of preparing compounds and compositions include incorporating the metal-organic compound into the material during an extrusion process. The resulting metal-organic compound and material blend is then used to coat or fabricate devices by traditional fabrication methods.

According to various embodiments of the present disclosure, a one or a multi-step method could be used to fabricate the device or device coating. For example, a base material layer may be applied to a substrate by traditional engineering methods that, various embodiments, does not contain either a metal-organic compound or a secondary therapeutic agent; contains either a metal-organic compound or a secondary therapeutic agent; or contains both a metal-organic compound or a secondary therapeutic agent.

In still other embodiments, the base layer is followed by a second material layer that does not contain either a metal-organic compound or secondary therapeutic agents; contains either a metal-organic compound or a secondary therapeutic agents; or contains both a metal-organic compound or therapeutic agents.

In other embodiments, the second layer is followed by a subsequent material layer that does not contain either a metal-organic compound or secondary therapeutic agents; contains either a metal-organic compound or secondary therapeutic agents; or contains both a metal-organic compound or secondary therapeutic agents.

Additional layers may be applied that do not contain either a metal-organic compound or secondary therapeutic agents; contains either a metal-organic compound, or secondary therapeutic agents; or contains both a metal-organic compound or secondary therapeutic agents.

In various embodiments, biodegradable polymers may be formed with metal-organic compounds blended into the open spaces of the polymers during formation. Metal-organic compounds may be encapsulated within a material to form nanoparticles or microparticles for delivery to the site of need.

VI. Devices and Methods of Using Compounds and Compositions

The present disclosure provides methods for producing nitric oxide comprising (i) providing a composition comprising a metal-organic framework, and (ii) exposing the composition to a nitric oxide-releasing compound. In various embodiments the metal-organic framework has a repeating structure in 1-dimension, 2-dimensions, 3-dimensions, or a mixture thereof. In some embodiments, the nitric oxide-releasing compound comprises a functional group selected from the group consisting of S-nitrosothiol, diazeniumdiolate, nitrate, nitrite, nitroso, and nitrosyl. Other functional groups capable of releasing nitric oxide can also be used.

In various embodiments, the exposing step comprises contacting the composition with fluids, tissues, or cells. In some embodiments, the exposing step comprises contacting the composition with physiological fluids. In some embodiments, the exposing step comprises contacting the composition with blood. In some embodiments the nitric oxide-releasing compound is present in fluids, tissues, or cells. In some embodiments the nitric oxide-releasing compound is present in physiological fluids. In some embodiments the nitric oxide-releasing compound is present in blood.

The present disclosure also provides methods for producing nitric oxide comprising providing a composition comprising a metal-organic framework, wherein the metal-organic framework is covalently attached to a nitric oxide-releasing functional group. In various embodiments the metal-organic framework has a repeating structure in 1-dimension, 2-dimensions, 3-dimensions, or a mixture thereof. In various embodiments the nitric oxide-releasing functional group is selected from the group consisting of S-nitrosothiol, diazeniumdiolate, nitrate, nitrite, nitroso, and nitrosyl. In various embodiments the metal-organic framework comprises a polydentate organic linker selected from the group consisting of

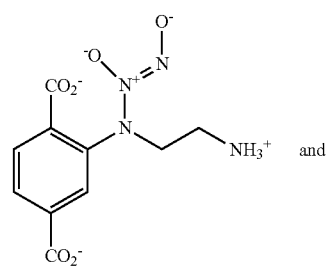

and

-continued

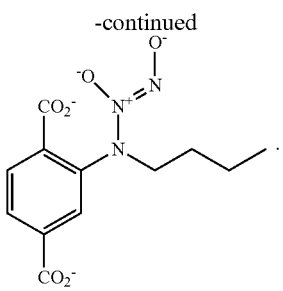

In various embodiments, the methods further comprise contacting the metal-organic frameworks having covalently attached nitric oxide-releasing functional groups with fluids, tissues or cells. In some embodiments, the methods further comprise contacting the metal-organic frameworks having covalently attached nitric oxide-releasing functional groups with physiological fluids. In some embodiments, the methods further comprise contacting the metal-organic frameworks having covalently attached nitric oxide-releasing functional groups with blood.

In various embodiments, the compositions, coatings, and medical devices disclosed herein produce nitric oxide for an extended period of time. The length (e.g., number of days) of the "extended period of time" will depend on the circumstances for which the compositions, coatings and/or medical devices are administered, as understood by those of ordinary skill in the art. By way of example, in various embodiments, the compositions, coatings, and medical devices disclosed herein produce nitric oxide for at least 1 day, at least 2 days, at least 3 days, at least 4 days, at least 5 days, at least 6 days, at least 7 days, at least 8 days, at least 9 days, at least 10 days, at least 11 days, at least 12 days, at least 13 days, at least 14 days, at least 3 weeks, at least 4 weeks, at least 5 weeks, at least 6 weeks, at least 7 weeks, and/or at least 8 weeks. In various embodiments, the compositions, coatings, and medical devices disclosed herein produce nitric oxide in an amount sufficient to treat a disease, disorder or condition, or to ameliorate one or more symptoms associated with a disease, disorder or condition. In various embodiments the compositions, coatings, and medical devices disclosed herein produce nitric oxide in an amount sufficient to promote wound healing and/or in amount sufficient to prevent platelet activation and adhesion.

Methods for treating diseases, disorders, or conditions in a patient using therapeutically effective amounts of the described compositions are provided in the present disclosure. As described herein, these diseases, disorders, or conditions may be present in the patient prior to treatment as well as caused by the procedure or the placement of the medical device. As used herein, "treatment" refers to the prevention of a disease or condition, the reduction or elimination of symptoms associated with a disease or condition, or the substantial or complete elimination of a disease or condition. Diseases, disorders or conditions, may include, but are not limited to, tumors, organs including the heart, coronary and peripheral vascular system (referred to overall as "the vasculature"), the urogenital system, including kidneys, bladder, urethra, ureters, prostate, vagina, uterus and ovaries, eyes, ears, spine, nervous system, lungs, trachea, esophagus, intestines, stomach, brain, liver and pancreas, skeletal muscle, smooth muscle, breast, dermal tissue, cartilage, tooth, bone, local infection, systemic infection, biofouling, macrophage formation, heart disease, artery and vein damage or disease, tissue injury, vascular legions, initimal hyperplasia, heart failure, high or elevated blood pressure, vasoconstriction, platelet adhesion, platelet aggregation, atherosclerosis, thrombo-embolism, thrombosis, smooth muscle cell proliferation, sepsis, complications with medical devices, wounds caused by incisions or insertion of medical devices, cicatrices, endothelial cell damage, arrhythmias, heart defects, congenital heart defects, cell overgrowth, and soft bones. In various embodiments, the compositions described herein are used to promote angiogenesis, delivery of analytes to the site of injury, and perfusion of blood to the site of injury. The compositions are also used to regulate the coagulation cascade.

Administration of the compositions of the present disclosure are administered, in various embodiments, as clinically prescribed including intravenously, orally, bucally, parenterally, inhalation spray, topically either within conjunction with a delivery vehicle (i.e., bandage or gel) or alone, locally, and transdermally. Local delivery includes any means by which the composition can be made in contact with the targeted delivery site in the patient including, but not limited, to, sutures, bandages, patches, wraps, vascular implants, stents, drug pumps, catheters, guidewires or any other implantable medical devices.

In still another embodiment, the disclosure provides a medical device that comprises a composition described herein. Such a medical device includes, without limitation, catheters (e.g., urological or vascular catheters such as balloon catheters and various central venous catheters), guide wires, balloons, filters (e.g., vena cava filters and mesh filters for distil protection devices), stents (including coronary vascular stents, peripheral vascular stents, cerebral, urethral, ureteral, biliary, tracheal, gastrointestinal, and esophageal stents), stent coverings, stent grafts, vascular grafts, abdominal aortic aneurysm (AAA) devices (e.g., AAA stents, AAA grafts), vascular access ports, dialysis ports, embolization devices including cerebral aneurysm filler coils (including Guglilmi detachable coils and metal coils), embolic agents, hermetic sealants, septal defect closure devices, myocardial plugs, patches, pacemakers, lead coatings including coatings for pacemaker leads, defibrillation leads, and coils, ventricular assist devices including left ventricular assist hearts and pumps, total artificial hearts, shunts, an interventional cardiology device, valves including heart valves and vascular valves, anastomosis clips and rings, cochlear implants, tissue bulking devices, and tissue engineering scaffolds for cartilage, bone, skin and other in vivo tissue regeneration, sutures, suture anchors, tissue staples and ligating clips at surgical sites, cannulae, metal wire ligatures, urethral slings, hernia, "meshes", artificial ligaments, orthopedic prosthesis such as bone grafts, bone plates, joint prostheses, orthopedic fixation devices such as interference screws in the ankle, knee, and hand areas, tacks for ligament attachment and meniscal repair, rods and pins for fracture fixation, screws and plates for craniomaxillofacial repair, dental implants, plastic tubing, a dialysis bag or membrane, a ventricular shunt, an external device applied directed to the skin as well as various other devices that are implanted or inserted into the body and from which therapeutic agent is released.

In various embodiments, the medical device is coated or completely fabricated from the matrices described herein.

In another embodiment of the present disclosure, a biocompatible stent is prepared by coating a metal organic compound containing polymer matrix with onto the surface of the stent. In another embodiment, PICC (peripherally inserted central catheter) lines are prepared by extruding a polyurethane with 0.5-50 wt. % Cu-BTC or Cu-BDC. In still another embodiment, vascular grafts which prevent thrombosis are fabricated by coating a PTFE polymer containing 0.5-50 wt. % Zn—(N,N-diazeniumdiolate-methylaminodicarboxylate).

EXAMPLES

Example 1

Materials and Instruments

Glutathione (GSH) and bis(2-ethylhexyl) sebacate, 97% were purchased from Acros Organics and used as received. Sodium nitrite, 97%, phosphate buffered saline (PBS) tablets and (ethylene dinitrilo) tetraacetic acid disodium salt, dehydrate (EDTA) were purchased from EMD Chemicals and used as received. High molecular weight poly(vinyl chloride) (PVC) was purchased from Aldrich. Tetrahydrofuran (THF), hydrochloric acid (HCl), acetone, and ethanol were purchased from Fisher and dried over 4 Å molecular sieves before use. Nitrogen and oxygen gases were supplied by Airgas.

UV-vis spectra were recorded using a Thermo Evolution 300 spectrophotometer. X-ray diffraction data were collected using a Scintag pXRD, equipped with a Cu x-ray source. Nitric oxide release profiles were obtained using a Sievers Nitric Oxide Analyzer (NOA), model 280i.

Example 2

Preparation of $CU_3$(1,3,5-benzenetricarboxylic acid)$_2$ $Cu_3$(1,3,5-benzenetricarboxylic acid)$_2$ ($Cu_3(BTC)_2$) crystals were synthesized according to literature procedures (Chui, S., et al., *Science*, 283:1149-1150, 1999) as follows. To a solution of $Cu(NO_3)_2.2.5$; $H_2O$ (0.4187 g; 1.8 mmol) in 6 mL deionized water was added 6 mL of an ethanol solution containing 0.2101 g (1.0 mmol) 1,3,5-benzene tricarboxylic acid (BTC). The reaction mixture was then added to a 12 mL Teflon liner in a Parr reaction vessel and heated under solvothermal conditions at 348 K for 20 hours. The resulting crystals were filtered from the reaction solution and washed three times with methanol and three times with deionized water. The materials were activated under vacuum at 373 K and stored in a dessicator until use.

Example 3

Preparation of Films Containing $Cu_3(BTC)_2$

To a solution of plasticized PVC (1 g; 33.3% PVC and 66.7% dioctyl sebacate) in 10 mL of THF was added 5% by weight of $Cu_3(BTC)_2$ crystals. The resulting mixture was vortexed until an even and fine blue-colored dispersion was obtained. An aliquot (2 mL) of the dispersion was added to a 20 mL glass beaker, and the solvent was allowed to evaporate to produce a circular film 3 cm in diameter and 0.250 mm thick.

Figure 6:
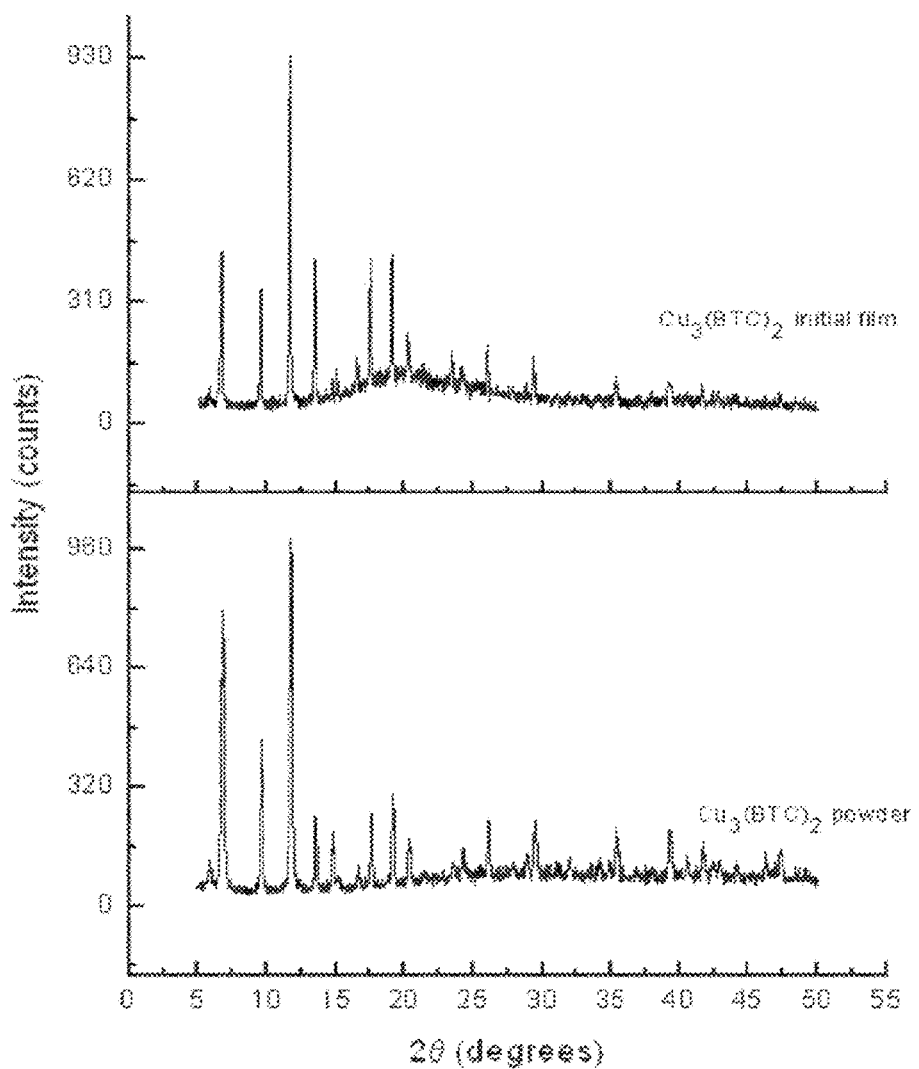
FIG. 6 is a graph showing pXRD spectra of $Cu_3(BTC)_2$ incorporated into a plasticized plasticized PVC (1:2 PVC:dioctyl sebacate) film (top) and $Cu_3(BTC)_2$ as a power (bottom).

To determine the stability of $Cu_3(BTC)_2$ incorporated in a plasticized PVC film compared to $Cu_3(BTC)_2$ powder, X-ray diffraction data of the film and of $Cu_3(BTC)_2$ powder were collected using a Scintag pXRD, equipped with a Cu x-ray source. As shown in FIG. 6, $Cu_3(BTC)_2$ incorporated in a plasticized PVC film demonstrated similar morphology compared to $Cu_3(BTC)_2$ powder. Thus, incorporation $Cu_3$(BTC)$_2$ in a polymer matrix preserved the structural integrity of the $Cu_3(BTC)_2$ framework.

Additional films were prepared according to the procedure described above, with the exception that the films (1) included different weight percentages of $Cu_3(BTC)_2$, or (2) included different ratios of PVC to dioctyl sebacate. Specifically, films were prepared using a PVC:dioctyl sebacate ratio of 1:1 and 5 wt. % $Cu_3(BTC)_2$; a PVC:dioctyl sebacate ratio of 2:1 and 5 wt. % $Cu_3(BTC)_2$; and a PVC:dioctyl sebacate ratio of 1:2 and 10 wt. % $Cu_3(BTC)_2$; a PVC:dioctyl sebacate ratio of 1:1 and 10 wt. % $Cu_3(BTC)_2$; a PVC:dioctyl sebacate ratio of 2:1 and 10 wt. % $Cu_3(BTC)_2$; and a PVC:dioctyl sebacate ratio of 1:2 and 20 wt. % $Cu_3(BTC)_2$. These additional films all demonstrated similar morphology compared to $Cu_3(BTC)_2$ powder, as determined by X-ray diffraction analysis.

Example 4

Preparation of Coatings Containing $Cu_3(BTC)_2$ on a PVC Substrate

Films containing $Cu_3(BTC)_2$ were coated onto PVC substrates. Specifically, a dispersion of plasticized PVC (1:2 PVC:dioctyl sebacate) with 5 wt. % $Cu_3(BTC)_2$ was prepared according to the procedure described in Example 3. The dispersion was coated directly onto 1.85 cm sections of PVC tubing ($d_O$=0.0953 cm and $d_i$=0.635 cm; final surface area=10 cm$^2$) to obtain a PVC substrate having a coating containing $Cu_3(BTC)_2$ Example 5

Preparation of S-nitrosoglutathione

S-nitroglutathione (GSNO) was prepared by a previously described procedure (Hart T. W., *Tetrahedron Letters*, 26:2013-2016, 1985) as follows. A 30 mL amber vial was rinsed thoroughly with a 100 µM EDTA solution to remove any trace metal impurities on the glassware. Deionized water (8 mL) treated with 0.00194 g EDTA was added to the amber vial. Glutathione (GSH) (1.536 g) was as added to the solution and acidified with 2.5 mL of 2 M HCl. The solution was placed in an ice water bath and continuously stirred until the GSH fully dissolved. To the stirred solution, $NaNO_2$ (0.414 g; 1.2 equiv.) was added. The solution immediately turned bright red, which is characteristic of GSNO formation. The solution was allowed to continue stirring in the ice bath for an additional 40 minutes to allow the reaction to reach completion. 10 mL of acetone was then added to the cold solution and allowed to stir for an additional ten minutes. The red GSNO precipitate was isolated by filtration and thoroughly washed three times with acetone for a final yield of 45%. Characterization of the material was investigated by UV-vis spectroscopy with identification of characteristic absorbance value at 335 nm ($\varepsilon$=922 M$^{-1}$ cm$^{-1}$).

Example 6

Nitric Oxide Release from Films Containing $Cu_3(BTC)_2$

Nitrc oxide release measurements from films containing $Cu_3(BTC)_2$ were conducted via chemiluminescence detection using a Sievers Nitric Oxide Analyzer, model 280i. The sampling rate was set to 200 mL/min with a cell pressure of 5.3 Torr and an oxygen pressure of 5.6 psig. Data was collected every 5 seconds. Prior to each measurement, the instrument was calibrated using a zero gas ($N_2$) and a 45 ppm NO gas. To remove impurities, the gas was scrubbed through a potassium permanganate and charcoal filter.

NO measurements were performed by inserting a circular sample of film (approximately 0.9 cm in diameter) into a custom made sample cell containing 4 mL of PBS (pH 7.4) treated with 100 µM EDTA. The sample cell was sealed and continuously purged with a stream of ultrapure $N_2$ gas (99.999%). The sample cell was covered with aluminum foil to protect it from light and heated to 37° C. with a circulating water bath.

Figure 7:
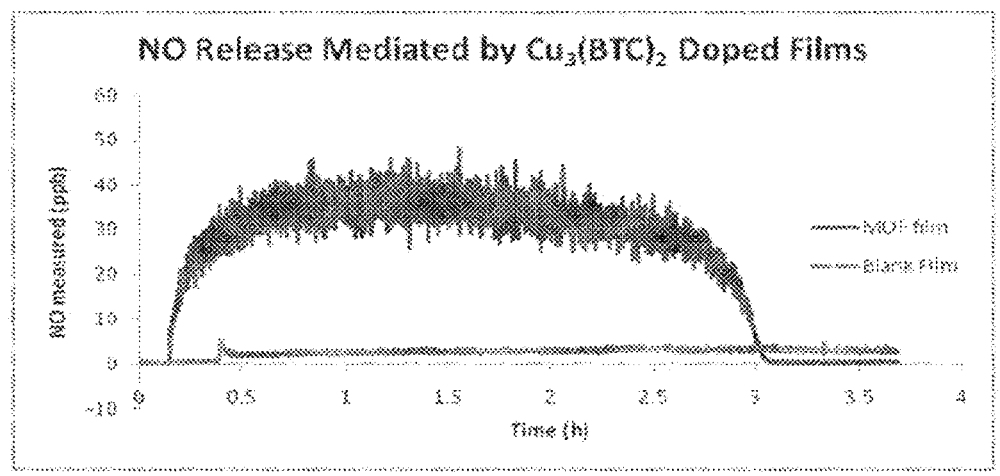
FIG. 7 is a graph showing nitric oxide release (ppb) from a plasticized PVC (1:2 PVC:dioctyl sebacate) film containing 5 wt. % $Cu_3(BTC)_2$ ("MOF film") compared to a film containing only plasticized PVC ("Blank film").

After 5 minutes, a 120 µL aliquot of 1 mM glutathione (GSM) was added directly to the solution using a glass syringe via a side injection port on the sample cell. Once a stable baseline reading was obtained, an aliquot of a stock S-nitrosoglutathione (GSNO) solution was added to the sample cell to a final solution concentration of 10 µM GSNO, corresponding to a ratio of GSNO:GSH of 1:3. The moles of nitric oxide detected from each sample were determined using an instrument specific calibration constant of $1.8 \times 10^{-13}$ mol NO $ppb^{-1}s^{-1}$ A plasticized PVC (1:2 PVC:dioctyl sebacate) film with 5 wt. % $Cu_3(BTC)_2$ was prepared according to the procedure described in Example 3. As shown in FIG. 7, a film containing plasticized PVC and $Cu_3(BTC)_2$ demonstrated a high level of nitric oxide release compared to a control film containing only plasticized PVC. Specifically, the film containing plasticized PVC and $Cu_3(BTC)_2$ demonstrated recovery of 92+2% of the theoretical amount of nitric oxide.

Example 7

Figure 8:
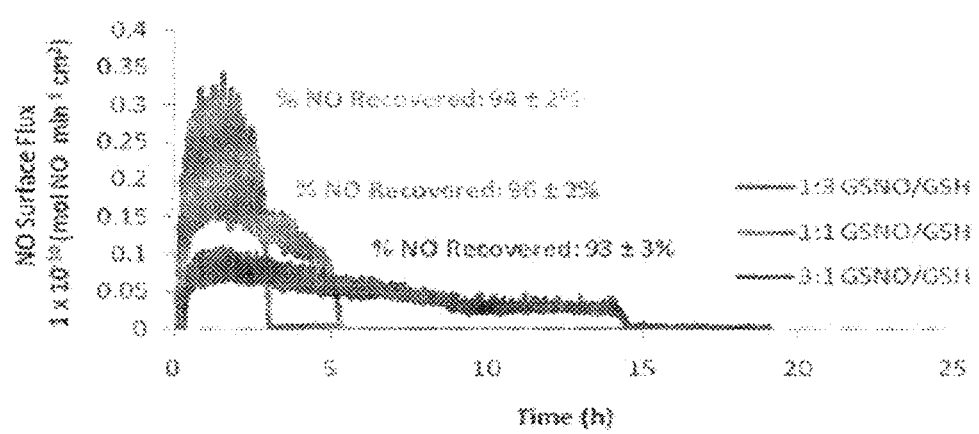
FIG. 8 is a graph showing nitric oxide surface flux ($1 \times 10^{-10}$ mol NO $min^{-1}$ $cm^2$) from a plasticized PVC (1:2 PVC:dioctyl sebacate) film containing 5 wt. % $Cu_3(BTC)_2$ in the presence of varying ratios of S-nitrosoglutathione (GSNO) to glutathione (GSH).

Nitric Oxide Release From Films Containing $Cu_3(BTC)_2$ in the Presence of Varying Substrate Concentrations Nitric oxide release measurements from films containing $Cu_3(BTC)_2$ were conducted according to the procedure described in Example 6, with the exception that different ratios of S-nitrosoglutathione (GSNO) to glutathione (GSH) worn used. Specifically, GSNO:GSH ratios of 1:3, 1:1 and 3:1 were used. To normalize for variations in the surface area of the samples, nitric oxide surface flux (moles of nitric oxide produced per surface area of the material as a function of time) was calculated. As shown in FIG. 8, different nitric oxide surface flux profiles are demonstrated when different GSNO:GSH ratios are used. Thus, the release rate of nitric oxide from films containing $Cu_3(BTC)_2$ can be controlled by varying the amount of GSH in solution relative to the amount of GSNO.

Example 8

Preparation of and Nitric Oxide Release from Films Containing Cu-BTT

In a prophetic example, a film containing Cu-BTT is prepared according to the procedure described in Example 3, with the exception that Cu-BTT is added in place of $Cu_3$ $(BTC)_2$ X-ray diffraction data of the film and of Cu-BIT powder are collected using a Scintag pXRD, equipped with a Cu x-ray source. Cu-BTT incorporated in a plasticized PVC film demonstrates similar morphology compared to Cu-BIT powder. Thus, incorporation Cu-BTT in a polymer matrix preserves the structural integrity of the Cu-BTT framework.

Nitric oxide release measurements from films containing Cu-BTT are conducted according to the procedure described in Example 6. A film containing plasticized PVC and Cu-BTT demonstrates a high level of nitric oxide release compared to a control film containing only plasticized PVC. Specifically, the film containing plasticized PVC and Cu-BTT demonstrates nearly complete recovery of the theoretical amount of nitric oxide.

Example 9

Preparation of Nitric Oxide-Producing Compounds

In a prophetic example, an NO-producing compound is prepared by reacting metal-organic compound (1) or (3) with NO gas to form diazeniumdiolate (2) or (4), respectively, as shown in Schemes 1 and 2:

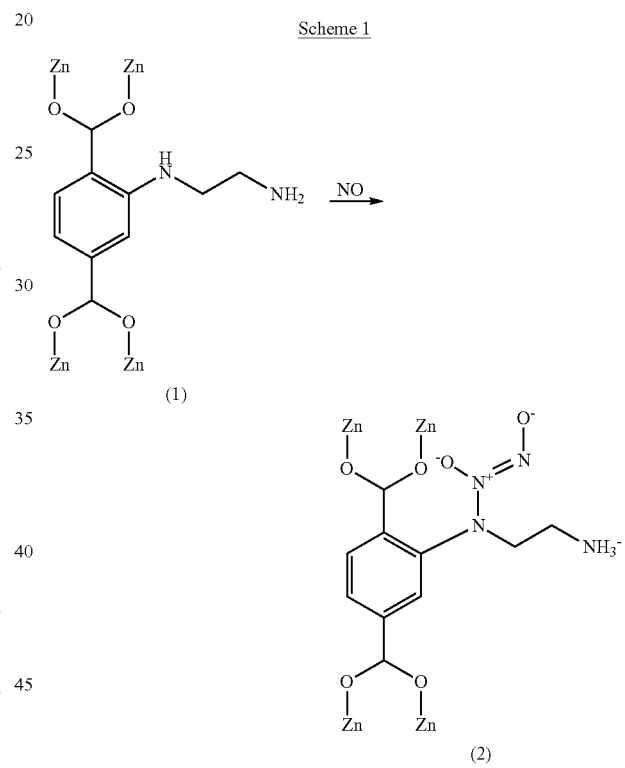

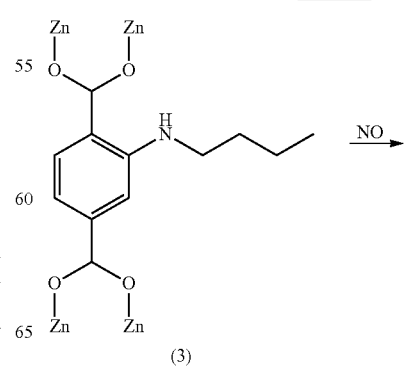

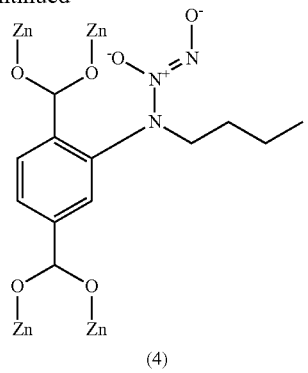

(4)

Example 10

Preparation of Nitric Oxide-Producing Matrices

In a prophetic example, an NO-donor matrix is prepared by first reacting 0.1 M zinc nitrate with N-methylaminobenzenedicarboxylic acid at 85° C. for 12 hours. The resulting metal-organic Zn—(N-methylaminobenzenedicarboxylate) is then reacted with NO gas at 80 psi for 24 hours to form a diazeniumdiolate function on the organic linker N atom. A polyurethane is prepared by blending 0.5-50 wt. % Zn—(N,N-diazeniumdiolate-methylaminobenzenedicarboxylate) into the polymer. When exposed to water under physiological conditions the resulting matrix produces NO.

In a prophetic example, NO-producing polymer matrices prepared by blending 0.5-50 wt. % Cu-BDC into poly(vinyl chloride) produce NO when exposed to S-nitrosothiol species under physiological conditions.

In a prophetic example, an NO-producing polymer matrix is prepared by blending 0.5-50 wt. % Cu-BPC into poly(vinyl chloride). This matrix produces NO when exposed to S-nitrosothiol species under physiological conditions.

In a prophetic example, an NO-producing polymer matrix is prepared by blending 0.5-50 wt. % Cu-BTC or Cu-BDC and heparin into poly(vinyl chloride). This composition produces NO when exposed to S-nitrosothiol species while simultaneously releasing heparin.

In a prophetic example, an NO-producing polymer matrix is prepared by blending 0.5-50 wt. % Cu-BTC or Cu-BDC into polyurethane. Heparin, a secondary therapeutic agent, is then chemically reacted with backbone of polyurethane. This composition produces NO when exposed to S-nitrosothiol species under physiological conditions.

In a prophetic example, an NO-donor matrix is prepared by blending 0.5-50 wt. % of metal-organic Zn—(N,N-diazeniumdiolate-methylaminobenzenedicarboxylate) with poly(lactic acid). As the matrix is exposed to water under physiological conditions, the NO is released and the poly(lactic acid) biodegrades.

In a prophetic example, an NO-donor matrix is prepared by blending 0.5-50 wt. % of metal-organic Zn—(N,N-diazeniumdiolate-methylaminobenzenedicarboxylate) with poly(lactic acid) and heparin as a secondary therapeutic agent. As the matrix is exposed to water under physiological conditions, the NO and the heparin are released and the poly(lactic acid) biodegrades.

In a prophetic example, an NO-producing matrix is prepared by reacting Cu-BTC with lactide while heating to produce a hybrid Cu-BTC and polylactide matrix. When exposed to physiological conditions, the polylactide component of the matrix decomposes to expose open copper metal sites of the Cu-BTC. These open copper sites then produce NO by reaction with S-nitrosothiol species present in the physiological fluid.

What is claimed is:

1. A method of forming a metal-organic compound containing polymer matrix, the method comprising:
    exposing a polymer in the presence of an organic solvent to a three-dimensional metal-organic framework to form a metal-organic compound containing polymer matrix; and
    drying the metal-organic compound containing polymer matrix, wherein the metal-organic compound containing polymer matrix is configured to continuously produce nitric oxide when exposed to a physiological fluid including a nitric oxide-releasing compound via a catalytic reaction catalyzed by the three-dimensional metal-organic framework, and wherein the three-dimensional metal-organic framework includes a polydentate organic linker having the formula

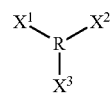

wherein $X^1$, $X^2$ and $X^3$ are nitrogen-containing heteroaromatic compounds selected from the group consisting of triazoyl and tetrazoyl;
R is an aromatic compound selected from the group consisting of benzene and naphthalene, wherein the benzene and naphthalene are substituted or unsubstituted; and wherein the three-dimensional metal-organic framework includes a metal selected from the group consisting of copper, zinc, iron, cobalt, manganese, vanadium, molybdenum, tungsten, chromium, nickel, aluminum and mixtures thereof; and
a nitric-oxide releasing functional group is covalently bound to the polydentate organic linker.

2. The method of claim 1 wherein $X^1$, $X^2$ and $X^3$ are triazolyls.

3. The method of claim 1 wherein $X^1$, $X^2$ and $X^3$ are tetrazoyls.

4. The method of claim 1, wherein the metal-organic framework has a porous structure comprising pores having an average size of about 5 Å to about 500 Å in diameter.

5. The method of claim 1, wherein the nitric oxide-releasing compound comprises a functional group selected from the group consisting of S-nitrosothiol, diazeniumdiolate, nitrate, nitrite, nitroso, and nitrosyl.

6. The method of claim 1, wherein the polymer is selected from the group consisting of poly(ε-caprolactone) and polyglycolide and mixtures and copolymers thereof.

7. The method of claim 1, wherein the polymer is selected from the group consisting of polyurethane (PU), polyesters, polyethers, silicones, silicates, poly(vinyl chloride) (PVC), acrylates, methacrylates, dextran, synthetic rubber (cis-polyisoprene), polyvinyl acetate, polyoxybenzylmethylenglycolanhydride (BAKELITE®), polychloroprene (NEOPRENE®), nylon, polystyrene, polyethylene, polypropylene, polyacrylonitrile, polyvinyl butyral (PVB), poly(vinylidene chloride), fluorinated polymers, polytetrafluoroethylene (PTFE), poly(ε-caprolactone), polyglycolide and mixtures and copolymers thereof.

8. The method of claim 1, wherein the metal is copper.

9. The method of claim 8, wherein $X^1$, $X^2$ and $X^3$ are tetrazoyls.

10. The method of claim 9, wherein R is benzene.

11. The method of claim 9, wherein R is naphthalene.

12. The method of claim 8, wherein $X^1$, $X^2$ and $X^3$ are triazolyls.

13. The method of claim 12, wherein R is benzene.

14. The method of claim 12, wherein R is naphthalene.

15. The method of claim 1, wherein the three-dimensional metal-organic framework is $Cu_3(1,3,5$-benzenetricarboxylic $acid)_2$.

16. The method of claim 1, wherein the three-dimensional metal-organic framework is Cu(1,3,5-benzenetristetrazolate).

* * * * *